(12) United States Patent
Wei et al.

(10) Patent No.: US 8,105,996 B2
(45) Date of Patent: Jan. 31, 2012

(54) MULTIPHASE PERSONAL CARE COMPOSITION COMPRISING A STRUCTURING

(75) Inventors: Karl Shiqing Wei, Mason, OH (US); Edward Dewey Smith, III, Mason, OH (US); Shawn Lynn Mansfield, Liberty Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 12/814,307

(22) Filed: Jun. 11, 2010

(65) Prior Publication Data

US 2011/0117225 A1 May 19, 2011

Related U.S. Application Data

(63) Continuation-in-part of application No. 12/054,853, filed on Mar. 25, 2008.

(60) Provisional application No. 60/921,210, filed on Mar. 30, 2007.

(51) Int. Cl.
*A61K 7/50* (2006.01)

(52) U.S. Cl. ........ 510/130; 510/121; 510/424; 510/426; 510/428; 510/475

(58) Field of Classification Search ................... None
See application file for complete search history.

(56) References Cited

U.S. PATENT DOCUMENTS

| | | | |
|---|---|---|---|
| 2,020,454 A | 11/1935 | Bisbee et al. | |
| 2,658,072 A | 11/1953 | Kosmin | |
| 2,986,271 A | 5/1961 | Forrer | |
| 3,455,440 A | 7/1969 | West | |
| 3,479,429 A | 11/1969 | Morshauser et al. | |
| 3,533,955 A | 10/1970 | Pader et al. | |
| 3,542,256 A | 11/1970 | Waterman | |
| 3,618,757 A | 11/1971 | Funkhouser | |
| 3,800,998 A | 4/1974 | Gask | |
| 3,850,365 A | 11/1974 | Dietrich | |
| 3,852,475 A | 12/1974 | Tarangul | |
| 3,899,076 A | 8/1975 | Florian | |

(Continued)

FOREIGN PATENT DOCUMENTS

CA 2246316 6/1998

(Continued)

OTHER PUBLICATIONS

International Search Report, PCT/US2008/058556, dated Oct. 22, 2010.

(Continued)

*Primary Examiner* — Necholus Ogden, Jr.

(57) ABSTRACT

The present invention relates to a personal care composition. The personal care composition comprises a surfactant phase. The surfactant phase comprises a surfactant of about 3% to about 12%, by weight of the personal care composition and a co-surfactant of about 4% or less by weight of the personal care composition. The surfactant includes sodium trideceth sulfate. The surfactant phase further comprises a structuring system. The structuring system comprises about 0.05% to about 5%, by weight of the personal care composition, of a crosslinked associative polymer and an electrolyte. The crosslinked associative polymer comprises a hydrophobic modification of less than 10% and can be hydrophobically modified with greater than a C6 alkyl. The personal care composition further comprises a benefit phase comprising a hydrophobic benefit material of about 1% to about 50%, by weight of the personal care composition.

20 Claims, 3 Drawing Sheets

U.S. PATENT DOCUMENTS

| | | |
|---|---|---|
| 3,929,678 A | 12/1975 | Laughlin et al. |
| 3,937,811 A | 2/1976 | Papantoniou et al. |
| 3,951,679 A | 4/1976 | Bernhard et al. |
| 3,980,767 A | 9/1976 | Chown et al. |
| 4,159,028 A | 6/1979 | Barker et al. |
| 4,263,363 A | 4/1981 | Buck et al. |
| 4,335,103 A | 6/1982 | Barker et al. |
| 4,379,753 A | 4/1983 | Bolich, Jr. |
| 4,425,322 A | 1/1984 | Harvey et al. |
| 4,518,578 A | 5/1985 | Hayes et al. |
| D292,879 S | 11/1987 | Smith |
| 4,966,205 A | 10/1990 | Tanaka |
| 4,980,155 A | 12/1990 | Shah et al. |
| 5,002,680 A | 3/1991 | Schmidt et al. |
| 5,059,414 A | 10/1991 | Dallal et al. |
| 5,223,315 A | 6/1993 | Katsura et al. |
| 5,228,189 A | 7/1993 | Driller et al. |
| 5,304,334 A | 4/1994 | Lahanas et al. |
| 5,393,450 A | 2/1995 | Shana'a |
| 5,455,035 A | 10/1995 | Guerrero et al. |
| 5,487,168 A | 1/1996 | Geiner et al. |
| 5,540,853 A | 7/1996 | Trinh et al. |
| 5,556,628 A | 9/1996 | Derian et al. |
| 5,578,299 A | 11/1996 | Starch |
| 5,612,307 A | 3/1997 | Chambers et al. |
| 5,632,420 A | 5/1997 | Lohrman et al. |
| 5,635,171 A | 6/1997 | Nadaud |
| 5,661,189 A | 8/1997 | Grievson et al. |
| 5,687,779 A | 11/1997 | Andersson et al. |
| 5,716,920 A | 2/1998 | Glenn et al. |
| 5,851,978 A | 12/1998 | Shana'a |
| 5,873,494 A | 2/1999 | Dallas, Jr. |
| 5,914,117 A | 6/1999 | Lavaud |
| 5,925,603 A | 7/1999 | D'Angelo |
| 5,929,019 A | 7/1999 | Puvvada et al. |
| 5,947,335 A | 9/1999 | Milio et al. |
| 5,952,286 A | 9/1999 | Puvvada et al. |
| 5,954,213 A | 9/1999 | Gerhart et al. |
| 5,965,500 A | 10/1999 | Puvvada |
| 5,965,501 A | 10/1999 | Rattinger et al. |
| 5,972,361 A | 10/1999 | Fowler et al. |
| D426,158 S | 6/2000 | Flurer et al. |
| 6,174,845 B1 | 1/2001 | Rattinger et al. |
| 6,176,391 B1 | 1/2001 | Rehkemper et al. |
| 6,176,395 B1 | 1/2001 | Abbott et al. |
| 6,190,648 B1 | 2/2001 | Kouzu et al. |
| 6,194,364 B1 | 2/2001 | Glenn, Jr. |
| D438,460 S | 3/2001 | Hammond |
| D439,165 S | 3/2001 | Erckelbout et al. |
| 6,213,166 B1 | 4/2001 | Thibiant et al. |
| D441,645 S | 5/2001 | Longhurst |
| 6,232,496 B1 | 5/2001 | Carr et al. |
| 6,245,323 B1 | 6/2001 | Christie et al. |
| 6,245,344 B1 | 6/2001 | Thibiant et al. |
| 6,268,322 B1 | 7/2001 | St. Lewis et al. |
| 6,306,806 B1 | 10/2001 | St. Lewis et al. |
| 6,335,312 B1 | 1/2002 | Coffindaffer et al. |
| 6,340,723 B1 | 1/2002 | Nitta et al. |
| D455,655 S | 4/2002 | Bunce |
| 6,367,519 B2 | 4/2002 | Thibiant |
| 6,383,999 B1 | 5/2002 | Coyle et al. |
| 6,385,992 B1 | 5/2002 | Flore, Jr. |
| 6,394,323 B2 | 5/2002 | McClean et al. |
| 6,419,783 B1 | 7/2002 | Rainey et al. |
| 6,426,326 B1 | 7/2002 | Mitra et al. |
| 6,429,177 B1 | 8/2002 | Williams et al. |
| 6,495,498 B2 | 12/2002 | Niemiec et al. |
| 6,506,391 B1 | 1/2003 | Biatry |
| 6,516,838 B2 | 2/2003 | Thibiant et al. |
| 6,517,939 B1 | 2/2003 | Moini et al. |
| 6,521,216 B1 | 2/2003 | Glendorf et al. |
| 6,534,456 B2 | 3/2003 | Hayward et al. |
| 6,534,457 B2 | 3/2003 | Mitra |
| 6,547,063 B1 | 4/2003 | Zaveri et al. |
| 6,555,509 B2 | 4/2003 | Abbas et al. |
| 6,564,978 B1 | 5/2003 | Safian et al. |
| 6,574,985 B2 | 6/2003 | Fiore, Jr. |
| 6,589,509 B2 | 7/2003 | Keller et al. |
| 6,652,134 B2 | 11/2003 | Lloyd |
| 6,663,855 B2 | 12/2003 | Frechet et al. |
| 6,673,371 B2 | 1/2004 | Brown et al. |
| 6,673,755 B2 | 1/2004 | Wei et al. |
| D486,395 S | 2/2004 | Lovell et al. |
| D486,398 S | 2/2004 | Lovell et al. |
| 6,691,394 B1 | 2/2004 | McClean |
| 6,695,510 B1 | 2/2004 | Look et al. |
| 6,759,376 B2 | 7/2004 | Zhang et al. |
| 6,780,826 B2 | 8/2004 | Zhang et al. |
| 6,924,256 B2 | 8/2005 | Massaro et al. |
| 7,143,893 B2 | 12/2006 | Kelly |
| 7,144,542 B2 | 12/2006 | Holzer et al. |
| 7,229,486 B2 | 6/2007 | Wiersema et al. |
| 7,273,837 B2 | 9/2007 | Boutique et al. |
| 7,511,003 B2 | 3/2009 | Focht et al. |
| 7,524,807 B2 | 4/2009 | Clapp et al. |
| 7,537,819 B2 | 5/2009 | Hendricks |
| 7,666,825 B2 | 2/2010 | Wagner et al. |
| 2003/0003069 A1 | 1/2003 | Carson et al. |
| 2003/0161852 A1 | 8/2003 | Miller et al. |
| 2003/0180246 A1 | 9/2003 | Frantz et al. |
| 2004/0028932 A1 | 2/2004 | Holzer et al. |
| 2004/0057920 A1 | 3/2004 | Focht et al. |
| 2004/0091445 A1 | 5/2004 | Dykstra et al. |
| 2004/0092425 A1 | 5/2004 | Boutique et al. |
| 2004/0105827 A1 | 6/2004 | Grimm et al. |
| 2004/0146475 A1 | 7/2004 | Peffly et al. |
| 2004/0158940 A1 | 8/2004 | Wells et al. |
| 2004/0180020 A1 | 9/2004 | Manelski et al. |
| 2004/0219119 A1 | 11/2004 | Wei et al. |
| 2004/0223929 A1 | 11/2004 | Clapp et al. |
| 2004/0223939 A1 | 11/2004 | Clausen et al. |
| 2004/0223991 A1 | 11/2004 | Wei et al. |
| 2004/0223992 A1 | 11/2004 | Clapp et al. |
| 2004/0232023 A1 | 11/2004 | Bansal et al. |
| 2004/0235693 A1 | 11/2004 | Wei et al. |
| 2004/0248748 A1* | 12/2004 | Wei et al. ................ 510/130 |
| 2004/0248749 A1 | 12/2004 | Mitra et al. |
| 2005/0003975 A1 | 1/2005 | Browne et al. |
| 2005/0020468 A1 | 1/2005 | Frantz et al. |
| 2005/0100570 A1 | 5/2005 | Wei et al. |
| 2005/0139574 A1 | 6/2005 | Simone et al. |
| 2005/0143269 A1 | 6/2005 | Wei et al. |
| 2005/0192187 A1 | 9/2005 | Wagner et al. |
| 2005/0192188 A1 | 9/2005 | Wagner et al. |
| 2005/0192189 A1 | 9/2005 | Wagner et al. |
| 2005/0238680 A1 | 10/2005 | Stella et al. |
| 2005/0249758 A1 | 11/2005 | Di Puccio Pagano |
| 2005/0269372 A1 | 12/2005 | Smith |
| 2005/0276768 A1 | 12/2005 | Wei et al. |
| 2006/0002880 A1 | 1/2006 | Peffly et al. |
| 2006/0008438 A1 | 1/2006 | Velarde et al. |
| 2006/0079419 A1 | 4/2006 | Wagner et al. |
| 2006/0079420 A1 | 4/2006 | Wagner et al. |
| 2006/0094628 A1 | 5/2006 | Wei et al. |
| 2006/0210505 A1 | 9/2006 | Clapp et al. |
| 2006/0276357 A1 | 12/2006 | Smith, III et al. |
| 2007/0141001 A1 | 6/2007 | Clapp et al. |
| 2007/0187274 A1 | 8/2007 | Dalea et al. |
| 2007/0248562 A1 | 10/2007 | Berry et al. |
| 2007/0280976 A1 | 12/2007 | Taylor et al. |
| 2010/0209374 A1 | 8/2010 | Wei et al. |

FOREIGN PATENT DOCUMENTS

| | | |
|---|---|---|
| DE | 196 50 952 A | 6/1998 |
| DE | 198 54 086 A | 5/2000 |
| EP | 0 078138 A2 | 5/1983 |
| EP | 0 331617 B | 4/1992 |
| EP | 1 108421 A2 | 6/2001 |
| EP | 1 005849 B1 | 9/2001 |
| EP | 1 064918 B1 | 9/2002 |
| EP | 0 907345 B1 | 5/2003 |
| JP | 2000229817 A | 8/2000 |
| JP | 2002-128639 A | 5/2002 |
| JP | 2002-138010 A | 5/2002 |
| WO | WO 90/13283 A1 | 11/1990 |
| WO | WO 94/10973 A1 | 5/1994 |
| WO | WO 97/17938 A1 | 5/1997 |

| | | | |
|---|---|---|---|
| WO | WO 98/27193 A1 | 6/1998 |
| WO | WO 99/38489 A1 | 8/1999 |
| WO | WO 99/38491 A1 | 8/1999 |
| WO | WO 00/75240 A1 | 12/2000 |
| WO | WO 01/01931 A1 | 1/2001 |
| WO | WO 01/23517 A1 | 4/2001 |
| WO | WO 01/70193 A2 | 9/2001 |
| WO | WO 01/70926 A1 | 9/2001 |
| WO | WO 02/100358 A1 | 12/2002 |
| WO | WO 03/055456 A1 | 7/2003 |
| WO | WO 03/105796 A1 | 12/2003 |
| WO | WO 2004/018609 A1 | 3/2004 |
| WO | WO 2004/026276 A1 | 4/2004 |
| WO | WO 2004/050055 A1 | 6/2004 |
| WO | WO 2005/016304 A1 | 2/2005 |
| WO | WO 2005/067875 A1 | 7/2005 |
| WO | 2006/042184 A1 | 4/2006 |
| WO | WO 2006/042176 A1 | 4/2006 |
| WO | WO 2006/042184 A1 | 4/2006 |

OTHER PUBLICATIONS

XP 002332778 "Dove All Day Moisturizing Body Wash" Online URL: http://www.ewg.org/reports/skindeep2/report.php?type=PRODUCT&id=8801874.

C.D. Vaughan, "Solubility, Effects in Product, in Package, Penetration and Preservation," Cosmetic and Toiletries, vol. 103, Oct. 1988.
Crank, Mathematics of Duffusion, $2^{nd}$ Edition, p. 63.
CTFA International Cosmetic Ingredient Dictionary, Fourth Edition, 1991, pp. 12 and 80.
Household Products Database, Brand Information, "Olay Daily Renewal Moisturizing Body Wash, Calming,"[Online] URL: http://householdproducts.nlm.nih.gov/cgi-bin/household/brands?tbl=brands&id=16003084, accessed Feb. 8, 2006 (2 pages).
Milton, Introduction to Probability and Statistics, $4^{th}$ Edition p. 317 (Section 9.2: Testing Hypotheses on a Proportion).
J. Caelles et al., "Anionic and Cationic Compounds in Mixed Systems,"Cosmetics & Toiletries, vol. 106, Apr. 1991. pp. 49-54.
C.J. van Oss, "Coacervation, Complex-Coacervation and Flocculation," J. Dispersion Science and Technology, vol. 9 (5, 6), 1988-89, p. 561-573.
D.J. Burgess, "Practical Analysis of Complex Coacervate Systems," J. of Colloid Anti Interface Science, vol. 140, No. 1, Nov. 1990, pp. 227-238.
KOBO Brochure, "Treated Pigments" (May 2000).

* cited by examiner

MULTIPHASE PERSONAL CARE COMPOSITION COMPRISING A STRUCTURING

CROSS REFERENCE TO RELATED APPLICATION(S)

This application is a continuation-in-part of U.S. application Ser. No. 12/054,853, filed on Mar. 25, 2008, which claims benefit of U.S. Provisional Application No. 60/921,210 filed on Mar. 30, 2007.

FIELD OF THE INVENTION

The present invention relates to a multiphase personal care composition that comprises an aqueous structured surfactant system, a structuring system and a benefit phase; wherein the structuring system comprises an associative polymer, and an electrolyte.

BACKGROUND OF THE INVENTION

Personal cleansing compositions that attempt to provide skin-conditioning benefits are known. Desirable personal cleansing compositions must meet a number of criteria. For example, in order to be acceptable to consumers, a multiphase personal cleansing composition must exhibit good cleaning properties, must exhibit good lathering characteristics, must be mild to the skin (not cause drying or irritation) and preferably should even provide a conditioning benefit to the skin Many personal cleansing compositions are aqueous systems that comprise emulsified conditioning oil or other skin conditioning agents, in combination with a lathering surfactant. Although these products provide both conditioning and cleansing benefits, it is often difficult to formulate a product that deposits sufficient amount of skin conditioning agents on skin during use. In order to combat emulsification of the skin conditioning agents by the cleansing surfactant, large amounts of the skin conditioning agent are added to the compositions. However, this introduces another problem associated with these cleansing and conditioning products. Raising the level of skin conditioning agent in order to achieve increased deposition may negatively affect the stability of the composition, as well as, speed of lather generation, total lather volume and overall product performance.

One way of counterbalancing the effect of raising the skin condition agents in personal care composition is to lower the level of the total surfactant in the personal care composition. Personal care compositions containing relatively low level of surfactants and having good lather properties are highly desired because the lower surfactant levels tend to make the composition milder, lower cost and easier to process. As well, lowering of the level of surfactant may increase deposition efficiency of skin conditioning agents, therefore may require less amount of skin conditioning agents that need to be added to the composition. However, with a decrease in surfactant level, the stability of the composition and the lather volume may be negatively impacted. FIG. 1 is a graph of Young's Modulus, a method of describing stability, as a function of percentage of lathering surfactant with a comparative personal care composition. As the level of lathering surfactant decreases in a composition, the stability of the composition is negatively impacted. Lowering the surfactant level in the composition may also change the overall structure of the composition, e.g. the composition may be a structured lamellar composition and when the surfactant level is lowered, the composition may become unstructured. FIG. 2 shows the lamellar phase volume of comparative personal care compositions as a function of percentage of lathering surfactant component in the cleansing phase. FIG. 2 shows that lamellar phase volume begins to decrease as the percentage of lathering surfactant component decrease and there is a significant drop below 16%, by weight of the surfactant phase, in a personal care composition.

Many types of stabilizers have used for structuring the surfactant phase of a composition. Cationic polymers such as Polymer JR® from Amerchol or Jaguar® from Rhone Poulenc, as disclosed in U.S. Pat. No. 3,580,853 to Parran et al, U.S. Pat. No. 5,085,857 to Reid et al., U.S. Pat. No. 5,439,682 to Wivell et al; or in WO 94/03152, WO 92/18100, or WO 97/48378. Another type of well-known suspension agents used to stabilize compositions with emollients are high molecular weight, water-soluble polymers such as polyacrylate, modified celluloses and guar polymers as disclosed broadly, for example, in U.S. Pat. No. 5,661,189 to Grieveson et al; U.S. Pat. No. 5,854,293 to R. W. Glenn, Jr; U.S. Pat. No. 5,905,062 to Elliott et al; U.S. Pat. No. 6,172,019 B1 to Dehan et al; and in U.S. Pat. No. 6,001,344 to Villa et al. using the combination of xanthan gum and Carbopol® as a novel structuring system for stable liquid cleansing composition. To stabilize the personal care compositions, high level of polymer is required which can in turn cause difficulty in processing and can impart an undesirable lumpy appearance and slimy feel during the use of the product.

Personal cleansing compositions containing fatty acids are widely described in the art such as in WO 94/17166 to Giret et al, WO 94/18737 to Cothran et al. U.S. Pat. No. 5,132,037 to Green et al., U.S. Pat. No. 5,234,619 to Green et al. and U.S. Pat. No. 5,290,470 to Green et al. These patents disclose the use of crystallized fatty acids either as skin benefit agents or as structuring agents. U.S. Pat. No. 5,360,580 to Rizvi et al teach the use of a long chain saturated fatty acid with polyethyleneamine to increase liquid stability. Liquid fatty acids such as oleic acid have been used as structurants to form lamellar structure with specific surfactant composition as described in U.S. Pat. Nos. 5,952,286 and 6,077,816 to Puvvada et al. As discussed more fully in the comparative examples below, FIG. 3 of the present application shows the minimal impact of fatty acid structurants on structure of the comparative examples of the present invention. To stabilize the composition, high levels of fatty acid structurants would be necessary. However, the use of increased levels of fatty acid structurants may negatively impact on lather volume, as shown in FIG. 3B of U.S. Pat. No. 6,906,016 issued to Villa. Moreover, personal care compositions have been made with structuring systems comprising specific water soluble/or swellable starch polymers combined with linear $C_8$ to $C_{13}$ fatty acids, such as in U.S. Pat. No. 6,906,016 issued to Villa. Such water swellable starch polymers would also have to be used at high levels which is costly and in some applications can affect lathering characteristics.

Accordingly, the need still remains for stable personal care composition that comprises low levels of surfactant, which are mild, structured, capable of producing abundant lather, and which also can deliver moisturizing or other active ingredients.

SUMMARY OF THE INVENTION

The present invention relates to a multiphase personal care composition. In one embodiment, the multiphase personal care composition comprises an aqueous structured surfactant phase, a structuring system and a benefit phase. The aqueous structured surfactant phase comprises from about 5% to about 16%, by weight of the multiphase personal care composition, of a lathering surfactant selected from the group comprising of anionic surfactants, nonionic surfactants, amphoteric surfactants, cationic surfactants or mixtures thereof and a structuring system. The structuring system can comprise a non-ionic emulsifier having an HLB of from about 1.4 to about 13; about 0.05% to about 5%, by weight of the multiphase personal care composition, of an associative polymer; and an electrolyte. The benefit phase comprises from about 1% to about 50%, by weight of the multiphase personal care composition, of hydrophobic benefit material.

According to another embodiment, the personal care composition comprises a surfactant phase and a benefit phase. The surfactant phase comprises of about 3% to about 12% by weight of the personal care composition of a surfactant. In one embodiment, the surfactant comprises sodium trideceth sulfate. The surfactant phase further comprises of about 4% or less by weight of the personal care composition of a co-surfactant and a structuring system. The structuring system comprises about 0.05% to about 5%, by weight of the personal care composition, of a crosslinked associative polymer and an electrolyte. The crosslinked associative polymer comprises a hydrophobic modification of less than 10% and can be hydrophobically modified with greater than a C6 alkyl. The benefit phase comprises from about 1% to about 50%, by weight of the multiphase personal care composition, of hydrophobic benefit material.

According to an example embodiment, the composition of the present invention comprises a lower level of surfactant which maintains acceptable structure, stability and rheology with excellent lather characteristics and skin benefits to multiphase personal care composition with higher surfactant levels. The composition comprises an associative polymer introduced into the surfactant phase. The inventors have found that a relatively low level of associative polymers builds rheological characteristics in the low surfactant systems, as shown in the inventive examples below, and maintains outstanding phase stability in the presence of skin conditioning agents without negatively impacting lathering characteristics The inventors have further found that a relatively low level of associative polymers in combination with non-ionic low HLB emulsifiers builds rheological characteristics in the low surfactant systems, as shown in FIG. 4 and FIG. 5 and the inventive examples below, and maintains outstanding phase stability in the presence of skin conditioning agents without negatively impacting lathering characteristics.

DETAILED DESCRIPTION OF THE INVENTION

Figure 1:
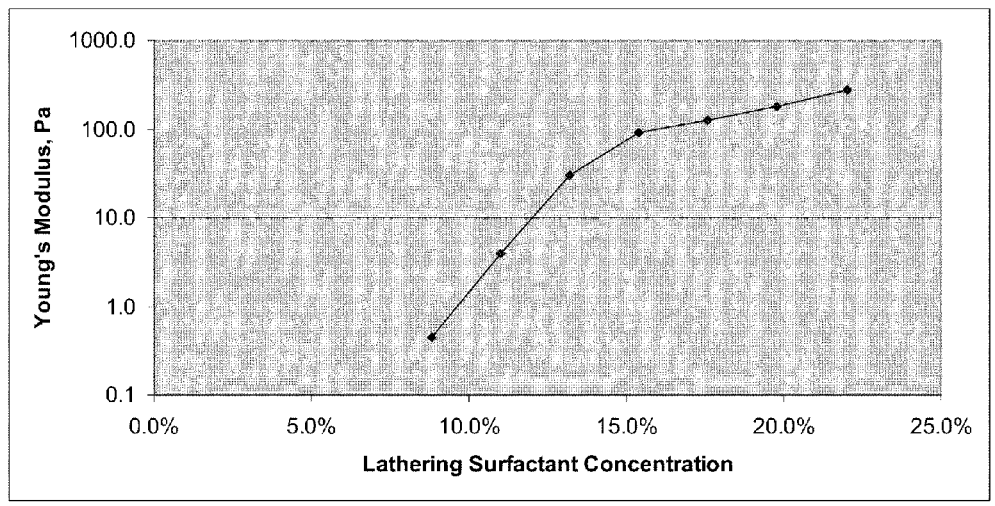
FIG. 1 is a graph that plots the Young's Modulus of the personal care compositions of comparative examples, as a function of percentage of lathering surfactant.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While the specification concludes with the claims particularly pointing and distinctly claiming the invention, it is believed that the present invention will be better understood from the following description.

The devices, apparatuses, methods, components, and/or compositions of the present invention can include, consist essentially of, or consist of, the components of the present invention as well as other ingredients described herein. As used herein, "consisting essentially of" means that the devices, apparatuses, methods, components, and/or compositions may include additional ingredients, but only if the additional ingredients do not materially alter the basic and novel characteristics of the claimed devices, apparatuses, methods, components, and/or compositions.

All percentages and ratios used herein are by weight of the total composition and all measurements made are at 25° C., unless otherwise designated. A degree is a planar unit of angular measure equal in magnitude to 1/360 of a complete revolution.

All measurements used herein are in metric units unless otherwise specified.

I. DEFINITIONS

The term "anhydrous" as used herein, unless otherwise specified, refers to those compositions or materials containing less than about 10%, more preferably less than about 5%, even more preferably less than about 3%, even more preferably zero percent, by weight of water.

The term "multiphase" as used herein means that compositions comprise at least two phases which are chemically distinct (e.g. a surfactant phase and a benefit phase). These phases are in direct physical contact with one another and are not separated by a barrier. In one aspect of the invention, phases of the multiphase personal care composition are blended or mixed to a significant degree. In another aspect of the invention, the phases of the multiphase personal care composition are made to occupy separate but distinct physical spaces inside the package in which they are stored, but are in direct contact with one another (i.e., they are not separated by a barrier and they are not emulsified or mixed to any significant degree). In one preferred embodiment of the present invention, the "multi-phase" personal care compositions comprise at least two visually distinct phases which are present within the container as a visually distinct pattern. The pattern results from the combination of the "multi-phase"

composition by a method of manufacture herein described. The "patterns" or "patterned" include but are not limited to the following examples: striped, marbled, rectilinear, interrupted striped, check, mottled, veined, clustered, speckled, geometric, spotted, ribbons, helical, swirl, arrayed, variegated, textured, grooved, ridged, waved, sinusoidal, spiral, twisted, curved, cycle, streaks, striated, contoured, anisotropic, laced, weave or woven, basket weave, spotted, and tessellated. Preferably the pattern is selected from the group consisting of striped, geometric, marbled, and combinations thereof.

In one aspect, the striped pattern can be relatively uniform across the dimension of the package. Alternatively, the striped pattern can be uneven, i.e. wavy, or can be non-uniform in dimension. The striped pattern does not need to necessarily extend across the entire dimension of the package. The size of the stripes can be at least about 0.1 mm in width and 10 mm in length, preferably at least about 1 mm in width and at least 20 mm in length as measured from the package exterior. The phases can be various different colors, and/or include particles, glitter or pearlescent agents in at least one of the phases in order to offset its appearance from the other phase(s) present.

The term "package" includes any suitable container for a personal care compositions exhibiting a viscosity from about 1,500 centipoise (cP) to about 1,000,000 cP, of including but not limited to bottle, tottle, tube, jar, non-aerosol pump and mixtures thereof.

The term "personal care composition" as used herein, refers to compositions intended for topical application to the skin or hair. The compositions of the present invention are rinse-off formulations, in which the product is applied topically to the skin or hair and then is subsequently rinsed within minutes from the skin or hair with water, or otherwise wiped off using a substrate with deposition of a portion of the composition. The compositions also may be used as shaving aids. The multiphase personal care composition of the present invention is typically extrudable or dispensible from a package. The multiphase personal care compositions typically exhibit a viscosity of from about 1,500 centipoise (cP) to about 1,000,000 cP, as measured by as measured by the Viscosity Method as described in the commonly owned, patent application published on Nov. 11, 2004 under U.S. Publication No. 2004/0223991A1 entitled "Multi-phase Personal Care Compositions" filed on May 7, 2004 by Wei, et al. The multiphase personal care compositions of the present invention can be in the form of liquid, semi-liquid, cream, lotion or gel compositions intended for topical application to skin. Examples of personal care compositions of the present invention can include but are not limited to shampoo, conditioning shampoo, body wash, moisturizing body wash, shower gels, skin cleansers, cleansing milks, hair and body wash, in shower body moisturizer, pet shampoo, shaving preparations and cleansing compositions used in conjunction with a disposable cleansing cloth.

The phrase "substantially free of" as used herein, unless otherwise specified means that the composition comprises less than about 5%, preferably less than about 3%, more preferably less than about 1% and most preferably less than about 0.1% of the stated ingredient. The term "free of" as used herein means that the composition comprise 0% of the stated ingredient that is the ingredient has not been added to the composition, however, these ingredients may incidentally form as a byproduct or a reaction product of the other components of the composition.

The term "stable," as used herein, means that the multiphase personal care composition comprises less than 5% "third-phase" volume, more preferably less than 2% "third-phase" volume, most preferably less than 1% "third-phase" volume after undergoing the rapid protocol aging and third phase measurement as described below in the "Third-Phase" Method.

The term "structured," as used herein means having a rheology that confers stability on the multiphase composition. The degree of structure is determined by characteristics determined by one or more of the following methods the Young's Modulus Method, Yield Stress Method, or the Zero Shear Viscosity Method or by the Ultracentrifugation Method, all in the Test Methods below. Accordingly, a surfactant phase of the multiphase composition of the present invention is considered "structured," if the surfactant phase has one or more of the following properties described below according to the Young's Modulus Method, Yield Stress Method, or the Zero Shear Viscosity Method or by the Ultracentrifugation Method. A surfactant phase is considered to be structured, if the phase has one or more of the following characteristics:

A. a Yield Stress of greater than about 0.1 Pascal (Pa), more preferably greater than about 0.5 Pa, even more preferably greater than about 1.0 Pa, still more preferably greater than about 2.0 Pa, still even more preferably greater than about 3 Pa, and even still even more preferably greater than about 5 Pa as measured by the Yield Stress and Zero Shear Viscosity Method described hereafter:

B. a Zero Shear Viscosity of at least about 500 Pascal-seconds (Pa-s), preferably at least about 1,000 Pa-s, more preferably at least about 1,500 Pa-s, even more preferably at least about 2,000 Pa-s; or C. a Structured Domain Volume Ratio as measured by the Ultracentrifugation Method described hereafter, of greater than about 40%, preferably at least about 45%, more preferably at least about 50%, more preferably at least about 55%, more preferably at least about 60%, more preferably at least about 65%, more preferably at least about 70%, more preferably at least about 75%, more preferably at least about 80%, even more preferably at least about 85%; or D. A Young's Modulus of greater than about 10 Pascal (Pa), more preferably greater than about 50 Pa, even more preferably greater than about 75 Pa, and still more preferably greater than 100 Pa.

The term "surfactant component" as used herein means the total of all anionic, nonionic, amphoteric, zwitterionic and cationic surfactants in a phase. When calculations are based on the surfactant component, water and electrolyte are excluded from the calculations involving the surfactant component, since surfactants as manufactured typically are diluted and neutralized.

The term "STS" as used herein, means sodium trideceth sulfate.

The term "ST3S" as used herein, means sodium trideceth sulfate, having an average number of moles of ethoxylate per molecule of 3, and trideceth derived from a 13 carbon branched hydrocarbon comprising preferably an average of at least 1 methyl branch per molecule.

The term "SLS" as used herein, means sodium laureth sulfate.

The term "lather" as used herein, means the aerated foam which results from providing energy to aqueous surfactant mixtures, especially dilute mixtures. Lather is increased in micellar compositions compared to structured, e.g., lamellar compositions, so that a phase change during dilution to micelles typically increases lather.

As used herein "tottle" refers to a bottle which rests on neck or mouth which its contents are filled in and dispensed from, but it is also the end upon which the bottle is intended to rest or sit upon (e.g., the bottle's base) for storage by the consumer and/or for display on the store shelf (this bottle is referred to herein as a "tottle"). Typically, the closure on a tottle is flat or concave, such that the tottle, when stored, rests on the closure. Suitable tottles are described in the co-pending U.S. patent application Ser. No. 11/067,443 filed on Feb. 25, 2005 to McCall, et al, entitled "Multi-phase Personal Care Compositions, Process for Making and Providing, and Article of Commerce."

The term "visually distinct" as used herein, refers to a region of the multiphase personal care composition having one average composition, as distinct from another region having a different average composition, wherein the regions are visible to the unaided naked eye. This would not preclude the distinct regions from comprising two similar phases where one phase could comprise pigments, dyes, particles, and various optional ingredients, hence a region of a different average composition. A phase generally occupies a space or spaces having dimensions larger than the colloidal or sub-colloidal components it comprises. A phase can also be constituted or re-constituted, collected, or separated into a bulk phase in order to observe its properties, e.g., by centrifugation, filtration or the like.

In one embodiment, the present invention relates to a personal care composition comprising: a surfactant phase comprising a surfactant of about 3% to about 12% by weight of the personal care composition, the surfactant comprising sodium trideceth sulfate; a co-surfactant of about 4% or less by weight of the personal care composition; and a structuring system comprising a crosslinked associative polymer of about 0.05% to about 5% by weight of the personal care composition, the crosslinked associative polymer comprising a hydrophobic modification of less than 10%, and the crosslinked associative polymer being hydrophobically modified with greater than a C6 alkyl; and an electrolyte. The personal care composition further comprises a benefit phase comprising a hydrophobic benefit material of about 1% to about 50%, by weight of the personal care composition.

Without wishing to be bound by theory, it is believed that the surprising and unexpected results produced by the personal compositions of the present invention eliminate the problems associated with personal care compositions. Specifically, it has been found that the use of STS in combination with a crosslinked associative polymer, enables increased structure at low concentrations. This structure allows for improved stability at lower surfactant levels. The reduction in surfactant improves compatibility of benefit agents within personal care compositions. The improved capability allows for additional benefit agents to be utilized in increased amounts. The reduction in surfactant, along with the increased capability of benefit agents, provides for increased mildness of personal care compositions. Finally, the improved structure allows for improved later at higher levels of dilution, as the micellar phase (where lather is capable of being formed) occurs at a higher level of dilution.

II. AQUEOUS STRUCTURED SURFACTANT PHASE

One of the phases of the multiphase personal care composition of the present invention is an aqueous structured surfactant phase. The surfactant phase is comprised of a structured domain that comprises surfactants. The structured domain is preferable an opaque structured domain, which is preferably a lamellar phase. The lamellar phase produces a lamellar gel network. The lamellar phase can provide resistance to shear, adequate yield to suspend particles and droplets and at the same time provides long term stability, since it is thermodynamically stable. The lamellar phase tends to have a viscosity that minimizes the need for viscosity modifiers.

a. Lathering Surfactants

The aqueous structured surfactant phase preferably comprises a surfactant component which comprises a mixture of lathering surfactants. The structured surfactant phase comprises surfactants suitable for application to the skin or hair. Suitable surfactants for use herein include any known or otherwise effective surfactant suitable for application to the skin, and which are otherwise compatible with the other essential ingredients in the multiphase personal care composition including water. These surfactants include anionic, nonionic, cationic, zwitterionic, amphoteric surfactants, soap, or combinations thereof. The multiphase personal care composition comprises from about 3% to about 16%, from about 10% to about 16%, from about 13% to about 15%, by weight of the multiphase personal care composition, of lathering surfactants selected from the group consisting of anionic surfactants, nonionic surfactants, amphoteric surfactants, cationic surfactants or mixtures thereof.

Suitable surfactants are described in McCutcheon's, Detergents and Emulsifiers, North American edition (1986), published by allured Publishing Corporation; and McCutcheon's, Functional Materials, North American Edition (1992); and in U.S. Pat. No. 3,929,678 issued to Laughlin, et al on Dec. 30, 1975.

Preferred linear anionic surfactants for use in the structured surfactant phase of the multiphase, personal care composition include ammonium lauryl sulfate, ammonium laureth sulfate, sodium lauryl sulfate, sodium laureth sulfate, potassium laureth sulfate, sodium lauryl sarcosinate, sodium lauroyl sarcosinate, lauryl sarcosine, cocoyl sarcosine, ammonium cocoyl sulfate, potassium lauryl sulfate, and combinations thereof.

Branched anionic surfactants and monomethyl branched anionic surfactants suitable for the present invention are described in a commonly owned, patent application published on December, 2006 under U.S. Publication No. 60/680,149 entitled "Structured Multi-phased Personal Cleansing Compositions Comprising Branched Anionic Surfactants" filed on May 12, 2005 by Smith, et al. Branched anionic surfactants include but are not limited to the following surfactants: sodium trideceth sulfate, sodium tridecyl sulfate, sodium $C_{12-13}$ alkyl sulfate, and $C_{12-13}$ pareth sulfate and sodium $C_{12-13}$ pareth-n sulfate.

For example, in one embodiment, the surfactant used in the personal care composition is sodium trideceth sulfate, hereinafter STS, including ST3S. The personal care compositions of the present invention comprise from about 3% to about 16% STS, alternatively from about 3% to about 13%, alternatively from about 5% to about 15% STS, alternatively from about 7% to about 13% STS, alternatively from about 5% to about 13% STS, alternatively from about 3% to about 12% STS, alternatively from about 1% to about 13% STS.

In one aspect of the multiphase personal care compositions of the present invention may further comprise a co-surfactant. In one embodiment, the personal care compositions of the present invention comprise from about 5% or less, alternatively from about 4% or less, alternatively from about 3% or less co-surfactant. The co-surfactant can comprise an amphoteric surfactant, a zwitterionic surfactant and mixtures thereof. In one embodiment, the multiphase personal care composition can comprise at least one amphoteric surfactant. Amphoteric surfactant suitable for use in the present invention include those that are broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group, e.g., carboxy, sulfonate, sulfate, phosphate, or phosphonate. Examples of compounds falling within this definition are sodium 3-dodecyl-aminopropionate, sodium 3-dodecylaminopropane sulfonate, sodium lauryl sarcosinate, N-alkyltaurines such as the one prepared by reacting dodecylamine with sodium isethionate according to the teaching of U.S. Pat. No. 2,658,072, N-higher alkyl aspartic acids such as those produced according to the teaching of U.S. Pat. No. 2,438,091, and the products described in U.S. Pat. No. 2,528,378. In one aspect, the multiphase personal care composition can comprise an amphoteric surfactant that is selected from the group consisting of sodium lauroamphoacetate, sodium cocoamphoactetate, disodium lauroamphoacetate disodium cocodiamphoacetate, and mixtures thereof. Moreover, Amphoacetates and diamphoacetates can also be used.

Zwitterionic surfactants suitable for use include those that are broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. Zwitterionic surfactants suitable for use in the multiphase, personal care composition include betaines, including cocoamidopropyl betaine.

The multiphase personal care composition of the present invention is preferably free of alkyl amines and alkanolamide to ensure mildness of the composition to the skin. Additionally, in one embodiment, the personal care compositions of the present invention comprise less than about 5% SLS, alternatively less than about 4% SLS, alternatively less than about 3% SLS, alternatively less than about 2% SLS, alternatively less than about 1% SLS, alternatively between about 0.1% SLS and about 2% SLS, alternatively about 0% SLS. Without wishing to be bound by theory, it is believed that the presence of SLS increases the harshness of the personal care composition, negating at least in part the mildness benefits and/or the efficacy of the benefit agents within the personal care composition.

b. Structuring System

A key component of the multiphase personal care composition of the present invention is the structuring system that comprises a combination of an associative polymer; an electrolyte; and optionally a low HLB emulsifier.

i. Associative Polymer

The structured surfactant phase of comprises from about 0.05% to about 5%, by weight of the multiphase personal care composition of associative polymer. Associative polymers are polymers constituted by a hydrophilic main chain and hydrophobic side chains. Their behavior in solution is a result of competition between the hydrophobic and hydrophilic properties of their structure. The hydrophobic units tend to form aggregates constituting linkage points between the macromolecular chains. From a rheological viewpoint, associative water-soluble polymers have a very high viscosifying power in water and retain their viscosity well in a saline medium. In mixed polymer and surfactant systems, surfactant aggregates can form, which are stabilized by different types of interactions: electrostatic interactions, dipolar interactions, or hydrogen bonds. Associative water-soluble polymers can interact more specifically with surfactants due to their hydrophobic portions.

The hydrophilic main chain of these associative polymers can, in particular, result from polymerization of a hydrophilic monomer containing functions onto which hydrophobic chains can subsequently be grafted, for example acid functions. This method of preparing associative polymers is described in particular in the "Water Soluble Polymers", ACS Symposium Series 467, ed. Shalaby W Shalaby et al., Am. Chem. Soc. Washington (1991), pp. 82-200. However, a water-soluble polymer of natural origin, or a natural polymer rendered water-soluble by chemical modification, can also be used. Associative polymers can also be formed by copolymerization of hydrophilic monomers and hydrophobic monomers. These hydrophobic polymers, introduced into the reaction medium in a much smaller quantity than the hydrophilic polymers, generally comprise a fatty hydrocarbon chain. This method of preparation is described in the publication by S. Biggs et. al., J. Phys Chem. (1992, 96. pp 1505-11).

Examples of associative polymers are acrylic polymers, polyethers, and polyosidic chains which may be partially substituted. The hydrophilic main chain is constituted as described above by a succession of hydrophilic monomer units and a fraction of monomers carrying highly hydrophobic pendant groups. The molar percentage of monomers carrying hydrophobic pendant groups is termed the modification percentage of the hydrophilic chain. The hydrophobic pendant groups can be any hydrophobic pendant group which is conventionally used to prepare associative polymers. On one aspect, the hydrophobic groups used comprise a backbone containing at least 8 carbon atoms, preferably 10 to 28 carbon atoms.

Particular examples of these hydrophobic groups are linear, branched, saturated or unsaturated hydrocarbon chains which may or may not contain cycles. Preferred examples of hydrophobic groups are hydrocarbon chains, in particular alkyl chains, containing 8 to 28 carbon atoms, preferably 12 to 22 carbon atoms. Modified units are advantageously in the form of an ether, ester or amide. This is particularly the case when the main chain of the associative polymer is an acrylic chain. The associative polymers used in the process of the invention can have a mass average molar mass in the range $10^4$ to $10^7$.

The concentration of associative polymer in the multiphase personal care composition is generally in the range about 0.05% to about 5, from about 0.25% to about 1.0%, by weight, from about 0.1% to about 2%, by weight, from about 0.1% to about 0.5% by weigh of the multiphase personal care composition. Preferred associative polymers includes hydrophobically modified polyacrylates; hydrophobically modified polysaccharides, hydrophobically modified urethanes. Non-limiting examples of associative polymers include Acrylates/Vinyl Isodecanoate Crosspolymer (Stabylen 30 from 3V), Acrylates/C10-30 Alkyl Acrylate Crosspolymer (Pemulen TR1 and TR2), Ammonium Acryloyldimethyltaurate/Beheneth-25 Methacrylate Crosspolymer (Aristoflex HMB from Clariant), Arylates/Beheneth-25 Methacrylate Copolymer (Aculyn 28 from Rohm and Haas); Acrylates/Steareth-20 Methacrylate Copolymer (Aculyn 22 from Rohm and Haas), PEG-150/Decyl Alclhol/SMDI Copolymer (Aculyn 44 from Rohm and Haas), PEG-150 Distearate (Aculyn 60 from Rohm and Haas), Acylates/Steareth-20 Methacrylate Crosspolymer (Aculyn 88 from Rohm and Haas).

In one embodiment, the associative polymer is a crosslinked alkali swellable, associative polymer comprising acidic monomers and associative monomers with hydrophobic end groups, where the polymer comprises a percentage hydrophobic modification and a hydrophobic side chain comprising alkyl functional groups having a length. Without intending to be limited by theory, it is believed that the acidic monomers contribute to the ability of the polymer to swell in water upon neutralization of the acidic groups; and associative monomers anchor the polymer into structured surfactant hydrophobic domains, e.g., lamellae, to confer structure to the surfactant compositions and keep the polymer from collapsing and losing effectiveness in the presence of electrolyte. The crosslinked associative polymer comprises a percentage hydrophobic modification, which is the mole percentage of monomers expressed as a percentage of the total number of all monomers in the polymer backbone, including both acidic and other non-acidic monomers. The percentage hydrophobic modification of the polymer, hereafter % HM, can be determined by the ratio of monomers added during synthesis, or by analytical techniques such as proton nuclear magnetic resonance (NMR). The alkyl side chain length can be determined similarly. Monomers comprising only 2 or fewer alkyl hydrocarbons (e.g., ethyl, methyl) are not considered associative for the purposes of the present invention, all side chains having more than 2 carbons being associative. Associative alkyl side chains comprise for example butyl, propyl, stearyl, steareth, cetyl, lauryl, laureth, octyl, behenyl, beheneth, steareth, or other linear, branched, saturated or unsaturated alkyl or alketh hydrocarbon side chains.

It has been discovered that crosslinked associative polymers having preferred % HM and preferred carbon numbers of the hydrophobic end groups of the alkyl side chains provide significant enhancement of structure to structured surfactant compositions of the present invention, especially to inventive compositions comprising reduced levels of surfactant; and provide said structure at surprisingly low levels of polymer structurant. Concentrations of associative polymer of up to 5% or even 10% are taught in the art to obtain a sufficient amount structure, for example the exemplary compositions of U.S. Pat. Nos. 7,119,059 (Librizzi, et al) and 6,897,253 (Schmucker-Castner, et al). Inventors have found when the associative polymer % HM and the alkyl side chain number of carbons is optimized, structure of the aqueous structured surfactant phase is increased using less than 3 wt % associative polymer as a percentage of the aqueous structured surfactant phase, preferably less than 2%, more preferably less than 1%, and even only about 0.2% of the phase, as demonstrated by the inventive examples hereinbelow.

The acidic monomer can comprise any acid functional group, for example sulfate, sulfonate, carboxylate, phosphonate, or phosphate or mixtures of acid groups. In one embodiment, the acidic monomer comprises a carboxylate, alternatively the acidic monomer comprises an acrylate, including acrylic acid and/or methacrylic acid. The acidic monomer comprises a polymerizable structure, e.g., vinyl functionality. Mixtures of acidic monomers, for example acrylic acid and methacrylic acid monomer mixtures, can also be used.

The associative monomer comprises a hydrophobic end group and a polymerizable component, e.g., vinyl, which are attached. The hydrophobic end group can be attached to the polymerizable component, and, hence to the polymer chain, by different means but preferably is attached by an ether or ester or amide functionality, such as an alkyl acrylate or a vinyl alkanoate monomer. The hydrophobic end group can also be separated from the chain, for example by an alkoxy ligand such as an alkyl ether. In an example embodiment, the associative monomer comprises an alkyl ester, alternatively an alkyl (meth)acrylate, where (meth)acrylate is understood to mean either methyl acrylate or acrylate or mixtures of the two.

According to one embodiment, the hydrophobic end group of the associative polymer is incompatible with the aqueous phase of the composition and associates with the lathering surfactant hydrophobe components of the current invention. Without intending to be limited by theory, it is believed that the longer alkyl chains of the structuring polymer hydrophobe end groups increase incompatibility with the aqueous phase to enhance structure, whereas somewhat shorter alkyl chains having carbon numbers closely resembling lathering surfactant hydrophobes (e.g., 12 to 14 carbons) or multiples thereof (for bilayers, e.g.) are also effective, so a range of preferred materials balancing these opposing requirements, limited by solubility of the total molecule itself, is ideal. Polymers having short alkyl side chains, e.g., less than 6 carbons, are ineffective for the present invention. Inventors have discovered an ideal range of hydrophobic end group carbon numbers combined with an optimal percentage of hydrophobic monomers expressed as a percentage of the polymer backbone provides increased structure to the lathering, structured surfactant composition at low levels of polymer structurant.

In one embodiment, preferred associative polymers comprise about C16 (cetyl) alkyl hydrophobic side chains with about 0.7% hydrophobic modification, but the percentage hydrophobic modification can be up to the aqueous solubility limit in surfactant compositions, e.g., about 2%, about 5%, or about 10%. According to another embodiment, preferred associative polymers can comprise between about C16 to about C22 alkyl hydrophobic side chains. An exemplary preferred associative polymer is Aqupec SER-300 made by Sumitomo Seika of Japan, which is Acrylates/C10-30 alkyl acrylate crosspolymer and comprises stearyl side chains with less than about 1% HM. Other preferred associative polymers comprise stearyl, octyl, decyl and lauryl side chains. Preferred associative polymers are Aqupec SER-150 (acrylates/C10-30 alkyl acrylates crosspolymer) comprising about C18 (stearyl) side chains and about 0.4% HM, and Aqupec HV-701EDR which comprises about C8 (octyl) side chains and about 3.5% HM. Another preferred polymer is Stabylen 30 manufactured by 3V Sigma S.p.A., which is has branched isodecanoate hydrophobic associative side chains. Inventors have discovered not all crosslinked associative polymers are effective, and many are deleterious to structure. Associative polymers having hydrophobe side chains with fewer than about 7 carbons and having % HM greater than about 25% or about 50% are dispreferred. For example, Carbopol Aqua SF-1 (crosslinked acrylates copolymer) having average 4.5 carbon alkyl side chains and more than 50% HM is deleterious to structure as demonstrated by the examples hereinbelow.

ii. Non-Ionic Emulsifier

The multiphase personal care composition preferably comprises at least one nonionic emulsifier. Preferably the nonionic emulsifier has an HLB from about 1.5 to 13.0, preferably from about 3.4 to 13.0, more preferably 3.4 to about 9.5, more preferably 3.4 to about 8.0. The mild body wash composition preferably comprises a nonionic emulsifier at concentrations ranging from about 0.1% to about 10%, more preferably from about 0.25% to about 8%, even more preferably from about 0.5% to about 5%, still even more preferably from about 1.0% to about 3%, and still even still more preferably from about 1.5% to about 2.5%, by weight of the personal care compositions.

The balance between the hydrophilic and lipophilic moieties in a surfactant molecule is used as a method of classification (hydrophile-lipophile balance, HLB). The HLB values for commonly-used surfactants are readily available in the literature (e.g., HLB Index in *McCutcheon's Emulsifiers and Detergents*, MC Publishing Co., 2004). For example, cocamide monoethanolamine (CMEA) is known in the art to have an HLB value of 16.8. Another way of obtaining HLB values is to estimate by calculations. The HLB system was originally devised by Griffin (J. Soc. Cosmetic Chem., 1, 311, 1949). Griffin defined the HLB value of a surfactant as the mol % of the hydrophilic groups divided by 5, where a completely hydrophilic molecule (with no non-polar groups) had an HLB value of 20. Other examples of how to calculate HLB values are described by Davies in *Interfacial Phenomena*, 2nd Edition, Academic Press, London, 1963 and by Lin in *J. Phys. Chem.* 76, 2019-2013, 1972.

Non-limiting examples of preferred nonionic emulsifiers for use herein are those selected form the group consisting of glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, and mixtures thereof.

iii. Electrolyte

An electrolyte can be added per se to the multiphase personal care composition or it can be formed in situ via the counterions included in one of the raw materials. The electrolyte preferably includes an anion comprising phosphate, chloride, sulfate or citrate and a cation comprising sodium, ammonium, potassium, magnesium or mixtures thereof. Some preferred electrolytes are sodium chloride, ammonium chloride, sodium or ammonium sulfate. The electrolyte is preferably added to the structured surfactant phase of the composition in the amount of from about 0.1% to about 6% preferably from about 1% to about 5%, more preferably from about 2% to about 4%, more preferably from about 3% to about 4%, by weight of the multiphase personal care composition.

III. BENEFIT PHASE

The multiphase personal care compositions of the present invention comprise a benefit phase. The benefit phase in the present invention is preferably anhydrous and can be substantially free of water. The benefit phase can be substantially free or free of surfactant.

The benefit phase typically comprises hydrophobic benefit materials. The benefit phase may comprise from about 1% to about 50%, preferably from about 5% to about 30%, more preferably from about 10% to about 30%, by weight of the multiphase personal care composition, of a hydrophobic benefit material.

Hydrophobic benefit materials suitable for use in the present invention preferably have a Vaughan Solubility Parameter of from about 5 $(cal/cm^3)^{1/2}$ to about 15 $(cal/cm^3)^{1/2}$ as defined by *Vaughan in Cosmetics and Toiletries*, Vol. 103. The Vaughan Solubility Parameter (VSP) as used herein is a parameter used to define the solubility of hydrophobic materials. Vaughan Solubility parameters are well known in the various chemical and formulation arts and typically have a range of from 5 to 25. Non-limiting examples of hydrophobic benefit materials having VSP values ranging from about 5 to about 15 include the following: Cyclomethicone 5.92, Squalene 6.03, Petrolatum 7.33, Isopropyl Palmitate 7.78, Isopropyl Myristate 8.02, Castor Oil 8.90, Cholesterol 9.55, as reported in *Solubility, Effects in Product, Package, Penetration and Preservation*, C. D. Vaughan, Cosmetics and Toiletries, Vol. 103, October 1988.

The hydrophobic benefit materials for use in the benefit phase of the composition have a preferred rheology profile as defined by Consistency value (k) and Shear Index (n). The term "Consistency value" or "k" as used herein is a measure of lipid viscosity and is used in combination with Shear Index, to define viscosity for materials whose viscosity is a function of shear. The measurements are made at 35° C. and the units are poise (equal to 100 cps). The term "Shear Index" or "n" as used herein is a measure of lipid viscosity and is used in combination with Consistency value, to define viscosity for materials whose viscosity is a function of shear. The measurements are made at 35° C. and the units are dimensionless. Consistency value (k) and Shear Index (n) are more fully described in the Test Methods below. Preferred Consistency value ranges are 1-10,000 poise $(1/sec)^{n-1}$, preferably 10-2000 poise $(1/sec)^{n-1}$ and more preferably 50-1000 poise $(1/sec)^{n-1}$. Shear Index ranges are 0.1-0.8, preferably 0.1-0.5 and more preferably 0.20-0.4. These preferred rheological properties are especially useful in providing the personal cleansing compositions with improved deposition of benefit agents on skin.

The benefit phase can be comprised of the hydrophobic benefit materials selected from the group consisting of petrolatum, lanolin, derivatives of lanolin (e.g. lanolin oil, isopropyl lanolate, acetylated lanolin, acetylated lanolin alcohols, lanolin alcohol linoleate, lanolin alcohol riconoleate) hydrocarbon oils (e.g. mineral oil) natural and synthetic waxes (e.g. micro-crystalline waxes, paraffins, ozokerite, lanolin wax, lanolin alcohols, lanolin fatty acids, polyethylene, polybutene, polydecene, pentahydrosqualene) volatile or non-volatile organosiloxanes and their derivatives (e.g. dimethicones, cyclomethicones, alkyl siloxanes, polymethylsiloxanes, methylphenylpolysiloxanes), natural and synthetic triglycerides (e.g. castor oil, soy bean oil, sunflower seed oil, maleated soy bean oil, safflower oil, cotton seed oil, corn oil, walnut oil, peanut oil, olive oil, cod liver oil, almond oil, avocado oil, palm oil, sesame oil) and combinations thereof. In one aspect, at least about 50% by weight of the hydrophobic benefit materials are selected from the groups of petrolatum, mineral oil, paraffins, polyethylene, polybutene, polydecene, dimethicones, alkyl siloxanes, cyclomethicones, lanolin, lanolin oil, lanolin wax. The remainder of the hydrophobic benefit material can be selected from: isopropyl palmitate, cetyl riconoleate, octyl isononanoate, octyl palmitate, isocetyl stearate, hydroxylated milk glyceride and combinations thereof. The benefit phase of the multiphase personal care composition can be comprised a combination of petrolatum and mineral oil.

IV. OPTIONAL INGREDIENTS

While not essential for the purposes of the present invention, the non-limiting list of materials, in addition to the previously disclosed, optional materials, illustrated hereinafter are suitable for use in the multiphase personal care composition, and may be desirably incorporated in certain embodiments, for example to assist or enhance cleansing performance, for treatment of the skin, or to modify the aesthetics of the personal care composition as is the case with perfumes, colorants, dyes or the like. Optional materials useful in the products herein are categorized or described by their cosmetic and/or therapeutic benefit or their postulated mode of action or function. However, it is to be understood that the active and other materials useful herein can, in some instances, provide more than one cosmetic and/or therapeutic benefit or function or operate via more than one mode of action. Therefore, classifications herein are made for the sake of convenience and are not intended to limit an ingredient to the particularly stated application or applications listed. The precise nature of these optional materials, and levels of incorporation thereof, will depend on the physical form of the composition and the nature of the cleansing operation for which it is to be used. The optional materials are usually formulated at less than about less than about 6%, less than about 5%, less than about 4%, less than about 3%, less than about 2%, less than about 1%, less than about 0.5%, less than about 0.25%, less than about 0.1%, less than about 0.01%, less than about 0.005% of the multiphase personal care composition.

To further improve stability under stressful conditions such as high temperature and vibration, it is preferable to adjust the densities of the separate phases such that they are substantially equal. To achieve this, low density microspheres can be added to one or more phases of the personal care composition, preferably the structured surfactant phase. Multiphase personal care composition that comprises low density microspheres are described in a patent application published on May 13, 2004 under U.S. Patent Publication No. 2004/0092415A1 entitled "Striped Liquid Personal Cleansing Compositions Containing A Cleansing Phase and A Separate Phase with Improved Stability," filed on Oct. 31, 2003 by Focht, et al.

The phases of the multiphase personal care composition, preferably the structured surfactant phase, can further comprise a polymeric phase structurant. Non-limiting examples of polymeric phase structurant include but are not limited to the following examples: naturally derived polymers, synthetic polymers, crosslinked polymers, block copolymers, copolymers, hydrophilic polymers, nonionic polymers, anionic polymers, hydrophobic polymers, hydrophobically modified polymers, associative polymers, and oligomers.

The phases of the present compositions, preferably the structured surfactant phase, optionally can further comprise a liquid crystalline phase inducing structurant, which when present is at concentrations ranging from about 0.3% to about 15%, by weight of the phase. Suitable liquid crystalline phase inducing structurants include trihydroxystearin (available from Rheox, Inc. under the trade name THIXCIN® R). The multiphase personal care composition is free of fatty acid due to its negative impact on lather performance.

The multiphase personal care compositions of the present invention can additionally comprise an organic cationic deposition polymer in the one or more phases as a deposition aid for the benefit agents described herein. Suitable cationic deposition polymers for use in the compositions of the present invention contain cationic nitrogen-containing moieties such as quaternary ammonium moieties. Nonlimiting examples of cationic deposition polymers for use in the personal cleansing composition include polysaccharide polymers, such as cationic cellulose derivatives. Preferred cationic cellulose polymers are the salts of hydroxyethyl cellulose reacted with trimethyl ammonium substituted epoxide, referred to in the industry (CTFA) as Polyquaternium 10 which are available from Amerchol Corp. (Edison, N.J., USA) in their Polymer KG, JR and LR series of polymers with the most preferred being KG-30M. Other suitable cationic deposition polymers include cationic guar gum derivatives, such as guar hydroxypropyltrimonium chloride, specific examples of which include the Jaguar series (preferably Jaguar C-17) commercially available from Rhodia Inc., and N-Hance polymer series commercially available from Aqualon.

Other non limiting optional ingredients that can be used in the multiphase personal care composition of the present invention can comprise an optional benefit component that is selected from the group consisting of thickening agents; preservatives; antimicrobials; fragrances; chelators (e.g. such as those described in U.S. Pat. No. 5,487,884 issued to Bisset, et al.); sequestrants; vitamins (e.g. Retinol); vitamin derivatives (e.g. tocophenyl actetate, niacinamide, panthenol); sunscreens; desquamation actives (e.g. such as those described in U.S. Pat. Nos. 5,681,852 and 5,652,228 issued to Bisset); anti-wrinkle/anti-atrophy actives (e.g. N-acetyl derivatives, thiols, hydroxyl acids, phenol); anti-oxidants (e.g. ascorbic acid derivatives, tocophenol) skin soothing agents/skin healing agents (e.g. panthenoic acid derivatives, aloe vera, allantoin); skin lightening agents (e.g. kojic acid, arbutin, ascorbic acid derivatives) skin tanning agents (e.g. dihydroxyacteone); anti-acne medicaments; essential oils; sensates; pigments; colorants; pearlescent agents; interference pigments (e.g such as those disclosed in U.S. Pat. No. 6,395,691 issued to Liang Sheng Tsaur, U.S. Pat. No. 6,645,511 issued to Aronson, et al., U.S. Pat. No. 6,759,376 issued to Zhang, et al, U.S. Pat. No. 6,780,826 issued to Zhang, et al.) particles (e.g. talc, kolin, mica, smectite clay, cellulose powder, polysiloxane, silicas, carbonates, titanium dioxide, polyethylene beads) hydrophobically modified non-platelet particles (e.g. hydrophobically modified titanium dioxide and other materials described in a commonly owned, patent application published on Aug. 17, 2006 under Publication No. 2006/0182699A, entitled "Personal Care Compositions Containing Hydrophobically Modified Non-platelet particle filed on Feb. 15, 2005 by Taylor, et al.) and mixtures thereof. In one aspect, the multiphase personal care composition may comprise from about 0.1% to about 4%, by weight of the multiphase personal care composition, of hydrophobically modified titanium dioxide. One or more of the phases of the multiphase personal care composition can comprise a variety of additional optional ingredients such as shiny particles, beads, exfoliating beads. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992.

One or more of the phases of the multiphase personal care composition can comprise a variety of additional optional ingredients such as shiny particles, beads, exfoliating beads. Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992. Other optional ingredients are most typically those materials approved for use in cosmetics and that are described in the CTFA Cosmetic Ingredient Handbook, Second Edition, The Cosmetic, Toiletries, and Fragrance Association, Inc. 1988, 1992.

V. METHODS OF USE

The personal care compositions of the present invention are preferably applied topically to the desired area of the skin or hair in an amount sufficient to provide effective delivery of the skin cleansing agent, hydrophobic material, and particles to the applied surface. The compositions can be applied directly to the skin or indirectly via the use of a cleansing puff, washcloth, sponge or other implement. The compositions are preferably diluted with water prior to, during, or after topical application, and then subsequently the skin or hair rinsed or wiped off, preferably rinsed off of the applied surface using water or a water-insoluble substrate in combination with water. The present invention is therefore also directed to methods of cleansing the skin through the above-described application of the compositions of the present invention.

VI. METHOD OF MANUFACTURING

The multi-phase personal care compositions of the present invention may be prepared by any known or otherwise effective technique, suitable for making and formulating the desired multi-phase product form. It is also effective to combine toothpaste-tube filling technology with a spinning stage design. Additionally, the present invention can be prepared by the method and apparatus as disclosed in U.S. Pat. No. 6,213,166 issued to Thibiant, et al. The method and apparatus allows two or more compositions to be filled in a spiral configuration into a single container using at least two nozzles which fill the container, which is placed on a static mixer and spun as the composition is introduced into the container.

Alternatively, the present invention can be prepared by a method disclosed in commonly owned patent application published on Nov. 18, 2004 under U.S. Publication No. 2004/0219119 A1 entitled "Visually distinctive multiple liquid phase compositions" filed by Wei, et al. on Apr. 30, 2004. The method and apparatus allows two separate compositions to be combined in predetermined amounts, blended into a single resultant composition with visually distinct phases, and filled by one nozzle into a single container that is lowered and rotated during filling.

If the multi-phase personal care compositions are patterned, it can be desirable to be packaged as a personal care article. The personal care article would comprise these compositions in a transparent or translucent package such that the consumer can view the pattern through the package. Because of the viscosity of the subject compositions it may also be desirable to include instructions to the consumer to store the package upside down, on its cap to facilitate dispensing.

VII. EXAMPLES

The following examples further describe and demonstrate embodiments within the scope of the invention. The examples are given solely for the purpose of illustration and are not to be construed as limitations of the present invention, as many variations thereof are possible without departing from the spirit and scope of the invention.

Table 1, includes the formula of comparative example A. Comparative example A illustrates a typical structured cleansing phase composition with the total lathering surfactant component which is outside of the claimed ranges. The data shows that the formula of comparative example A exhibits lamellar structure and stability at least in part due to its high level of surfactant with Young's modulus of 273 Pa.

TABLE 1

| Comparative Example A | |
|---|---|
| | Comparative Example A |
| Total Lathering Surfactant Component (%) | 22.0 |
| Sodium Trideceth Sulfate [1] | 8.5 |
| Sodium Lauryl Sulfate [2] | 8.5 |
| Sodium Lauroamphoacetate [3] | 5.0 |
| Total Lamellar Phase Structurant (%) | 6.8 |
| Sodium Chloride | 4.8 |
| Trideceth-3 [4] | 2.0 |
| Skin Feel Polymers and Minors | |
| Guar hydroxypropyltrimonium chloride [5] | 0.6 |
| Xanthan gum [6] | 0.2 |
| Polyethylene oxide [7] | 0.1 |
| Methyl chloro isothiazolinone and methyl isothiazolinone [8] | 0.033 |
| EDTA [9] | 0.15 |

TABLE 1-continued

| Comparative Example A | |
|---|---|
| | Comparative Example A |
| Sodium Benzoate | 0.2 |
| Citric Acid, titrate | pH = 5.7 ± 0.2 |
| Water | Q.S. |

[1] sulfated from Iconol TDA-3 (available from BASF Corp.) to >95% sulfate;
[2] available from Procter & Gamble Co.;
[3] available from Cognis Chemical Corp.;
[4] Iconol TDA-3 available from BASF Corp.;
[5] N-Hance 3196 Polymer available from Aqualon;
[6] Keltrol 1000, available from Kelco Corp.;
[7] Polyox WSR301;
[8] Kathon CG, available from Rohm & Haas Company, Philadephia, PA;
[9] Dissolvine NA 2x.

TABLE 2

| Comparative Example A-0 to A-6 | | | | | | | |
|---|---|---|---|---|---|---|---|
| | A-0 | A-1 | A-2 | A-3 | A-4 | A-5 | A-6 |
| Dilution Factor in DI Water (%) | 100 | 90 | 80 | 70 | 60 | 50 | 40 |
| Total Lathering Surfactant Component (%) | 22.0 | 19.8 | 17.6 | 15.4 | 13.2 | 11 | 8.8 |
| Lamellar Phase Volume (%) | 79 | 77 | 76 | 72 | 0 | 0 | 0 |
| Young's Modulus (Pa)* | 273 | 181 | 127 | 90 | 30 | 4 | 0.5 |

*Target for Young's Modulus for compositions is > 100 Pa

Figure 2:
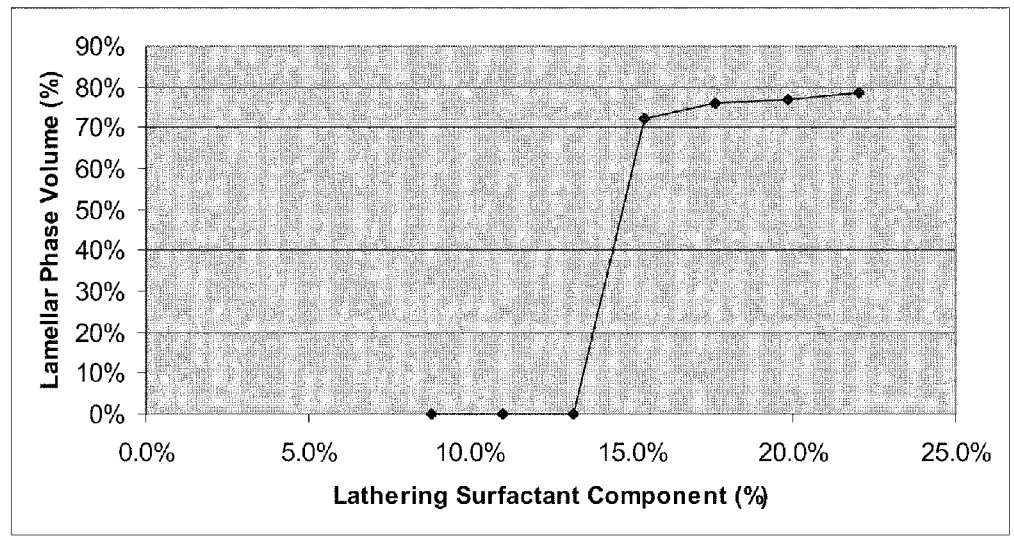
FIG. 2 is a graph that plots the lamellar phase volume of the personal care compositions of comparative examples, as a function of percentage of lathering surfactant component, by weight of the cleansing phase.

Table 2, includes the dilutions of comparative Example A. Comparative examples A0-A6 illustrate the effect of the level of lathering surfactant component on the cleansing phase structure upon water dilution of comparative example A. FIG. 1 is a graph that plots the Young's Modulus as a function of the percentage of lathering surfactant component of the personal care compositions in Table 2. The trend that is shown in FIG. 1 is that when the percentage of lathering surfactant decreases in the multiphase personal care composition the stability is negatively impacted. FIG. 2 is a graph the plots the lamellar phase volume as a function of percentage of lathering surfactant component of the personal care compositions in Table 2. The trend shown in the graph in FIG. 2 is that the lamellar phase volume begins to decrease as the percentage (level) of lathering surfactant in the composition is decreased. FIGS. 1 and 2 shows that there is a significant drop in lamellar phase volume and Young's modulus when the total lathering surfactant component is less than about 16%.

TABLE 3

| Comparative Examples A-3, B-3, C-3, D-3 and Example 1-3 of the Present Invention | | | | | | | |
|---|---|---|---|---|---|---|---|
| | Comparative Examples | | | | Inventive Examples | | |
| | A-3 | B-3 | C-3 | D-3 | 1 | 2 | 3 |
| Dilution Factor in DI Water (%) | 70 | 70 | 70 | 70 | 70 | 70 | 70 |
| Total Lathering Surfactant Component (%) | 15.4 | 15.4 | 15.4 | 15.4 | 15.4 | 15.4 | 15.4 |
| Lamellar Phase Structurant (%) | | | | | | | |
| Sodium Chloride | 3.3 | 4.8 | 3.3 | 3.3 | 3.3 | 3.3 | 3.3 |
| Trideceth-3 [1] | 1.4 | 1.4 | 2.4 | 1.4 | 1.4 | 1.4 | 1.4 |

TABLE 3-continued

Comparative Examples A-3, B-3, C-3, D-3 and Example 1-3 of the Present Invention

| | Comparative Examples | | | | Inventive Examples | | |
|---|---|---|---|---|---|---|---|
| | A-3 | B-3 | C-3 | D-3 | 1 | 2 | 3 |
| Associative Polymer | | | | | | | |
| Acrylates/Vinyl Isodecanoate cross polymer [2] | — | — | — | — | 1.0 | — | — |
| Acrylates/Beheneth-25 Methacrylate copolymer [3] | — | — | — | — | — | 1.0 | — |
| Acrylates/steareth-20 methacrylate crosspolymer [4] | — | — | — | — | — | — | 1.0 |
| Non-associative Polymer | | | | | | | |
| Acrylates copolymer [5] | — | — | — | 1.0 | — | — | — |
| Lamellar Phase Volume (%) | 72 | 76 | 78 | 40 | 92 | 64 | 47 |
| Young's Modulus (Pa) | 90 | 80 | 84 | 33 | 385 | 288 | 150 |

[1] Iconal TDA-3 available from BASF Corp.;
[2] Stabylen 30, available from 3V Company.
[3] Aculyn 28, available from Rohm and Hass Company, Philadelphia, PA;
[4] Aculyn 88, available from Rohm and Hass Company, Philadelphia, PA;
[5] Aculyn 33, available from Rohm and Hass Company, Philadelphia, PA.
*Target for Compositions of the Present Invention > 100 Pa.

Table 3 includes the formulas of the comparative examples A-3, B-3, C-3, D-3 and examples 1-3 of the present invention. Comparative example A3 has a formula with less than about % 16 surfactant and includes typical levels of lamellar structurants (sodium chloride and trideceth-3) and does not include associative and non-associative polymers. Comparative examples B3 and C3 include increasing levels of typical lamellar phase structurants (sodium chloride and trideceth-3). The data shows that there is no increase in Young's modulus when the surfactant level is lower than about 16% even with the increased level of lamellar phase structurants added in comparative example B3 and C3. The comparative example D3 illustrates that the conventional non-associative polymer is not effective at building lamellar structure and stability despite its common usage for thickening surfactant compositions. The inventive Examples 1-3 show that there is a significant increase in Young's modulus whenever associated polymers are incorporated in the lamellar phase cleansing composition.

TABLE 4

Comparative Examples A-4, B-4, C-4, D-4, and Inventive Example 4

| | Comparative Example | | | | Inventive Example |
|---|---|---|---|---|---|
| | A-4 | B-4 | C-4 | D-4 | 4 |
| Dilution Factor in DI Water (%) | 60 | 60 | 60 | 60 | 60 |
| Total Lathering Surfactant Component (%) | 13.2 | 13.2 | 13.2 | 13.2 | 13.2 |
| Lamellar Phase Structurant | | | | | |
| Sodium Chloride | 2.9 | 4.8 | 2.9 | 2.9 | 2.9 |
| Trideceth-3 (HLB = 8) [1] | 1.2 | 1.2 | 2.2 | 2.2 | 2.2 |
| Associative Polymer | | | | | |
| Acrylates/Vinyl Isodecanoate cross polymer [2] | — | — | — | — | 1.0 |
| Non-associative Polymer | | | | | |
| Acrylates copolymer [3] | — | — | — | 1.0 | — |
| Lamellar Phase Volume (%) | 0 | 75 | 71 | 24 | 40 |
| Young's Modulus (Pa) * | 30 | 43 | 55 | 25 | 207 |

[1] Iconal TDA-3 available from BASF Corp.;
[2] Stabylen 30 available from 3V;
[3] Aculyn 33 available from Rohm and Hass Company, Philadelphia, PA. Target for Compositions of the Present Invention >100 Pa.

Table 4 includes the formulas for comparative example A-4, B-4, C-4, D-4 and example 4 of the present invention. The formula of comparative example A4 is not stable and is not structured with a the formula that includes typical levels of lamellar structurants and no associative or non-associative polymer at 13% surfactant. Comparative examples B4 and C4 show that formulas that include higher levels of typical lamellar phase structurants (sodium chloride and trideceth-3) are not effective in increasing the Young's modulus while they do show an increase of lamellar phase volume. The example 4 of the present invention further illustrates the effectiveness of associative polymer in lamellar phase cleansing compositions when a total lathering surfactant at only 13%.

TABLE 5

Inventive Examples 5-7 and Comparative Examples E, F, G and H

| | Inventive Examples | | | Comparative Examples | | | |
|---|---|---|---|---|---|---|---|
| | 5 | 6 | 7 | E | F | G | H |
| I: Cleansing Phase Composition | | | | | | | |
| Total Lathering Surfactant Component in Cleansing Phase (%) | 15.4 | 15.4 | 15.4 | 15.4 | 15.4 | 15.4 | 15.4 |
| Sodium Trideceth Sulfate [1] | 5.9 | 5.9 | 5.9 | 5.9 | 5.9 | 5.9 | 5.9 |
| Sodium Lauryl Sulfate [2] | 5.9 | 5.9 | 5.9 | 5.9 | 5.9 | 5.9 | 5.9 |
| Sodium Lauroamphoacetate [3] | 3.6 | 3.6 | 3.6 | 3.6 | 3.6 | 3.6 | 3.6 |
| Associative Polymer (%) | | | | | | | |
| Acrylates/Vinyl Isodecanoate [4] | 0.25 | 0.5 | 0.75 | — | — | — | 0.25 |
| Fatty Acid Structurants (%) | | | | | | | |
| Lauric Acid | — | — | — | 1.0 | 2.0 | 3.0 | — |

TABLE 5-continued

Inventive Examples 5-7 and Comparative Examples E, F, G and H

|  | Inventive Examples | | | Comparative Examples | | | |
| --- | --- | --- | --- | --- | --- | --- | --- |
|  | 5 | 6 | 7 | E | F | G | H |
| Additional Lamellar Structrants (%) | | | | | | | |
| Sodium Chloride | 3.3 | 3.3 | 3.3 | 3.3 | 3.3 | 3.3 | 3.3 |
| Trideceth-3 (HLB = 8) [5] | 1.4 | 1.4 | 1.4 | 1.4 | 1.4 | 1.4 | — |
| Methyl chloro isothiazolinone and methyl isothiazolinone [6] | 0.033 | 0.033 | 0.033 | 0.033 | 0.033 | 0.033 | 0.033 |
| EDTA [7] | 0.15 | 0.15 | 0.15 | 0.15 | 0.15 | 0.15 | 0.15 |
| Sodium Benzoate | 0.2 | 0.2 | 0.2 | 0.2 | 0.2 | 0.2 | 0.2 |
| Citric Acid, titrate (pH = ±0.2) | 5.7 | 5.7 | 5.7 | 5.7 | 5.7 | 5.7 | 5.7 |
| Water | Q.S. | Q.S. | Q.S. | Q.S. | Q.S. | Q.S. | Q.S. |
| II: Benefit Phase Composition | | | | | | | |
| Petrolatum [8] | 70 | 70 | 70 | 70 | 70 | 70 | 70 |
| Mineral Oil [9] | 30 | 30 | 30 | 30 | 30 | 30 | 30 |
| III. Blending Ratio of Cleansing: Benefit Phase | 85:15 | 85:15 | 85:15 | 85:15 | 85:15 | 85:15 | 85:15 |
| Young's Modulus | 245 | 342 | 421 | 68 | 92 | 98 | 0.06* |

[1] sulfated from Iconol TDA-3, available from BASF Corp. to >95% sulfate;
[2] available from Procter & Gamble Co.;
[3] available from Cognis Chemical Corp.;
[4] Stabylen 30 available from 3V;
[5] Iconal TDA-3 available from BASF Corp.;
[6] Kathon CG, available from Rohm & Haas Company, Philadephia, PA;
[7] Dissolvine NA 2x.;
[8] G2218 from Sonnerbonn;
[9] Hydrobrite 1000 from Sonnerbonn

*Note:
Comparative example E was unstable at ambient and it showed split phases after one week at ambient.

Figure 4:
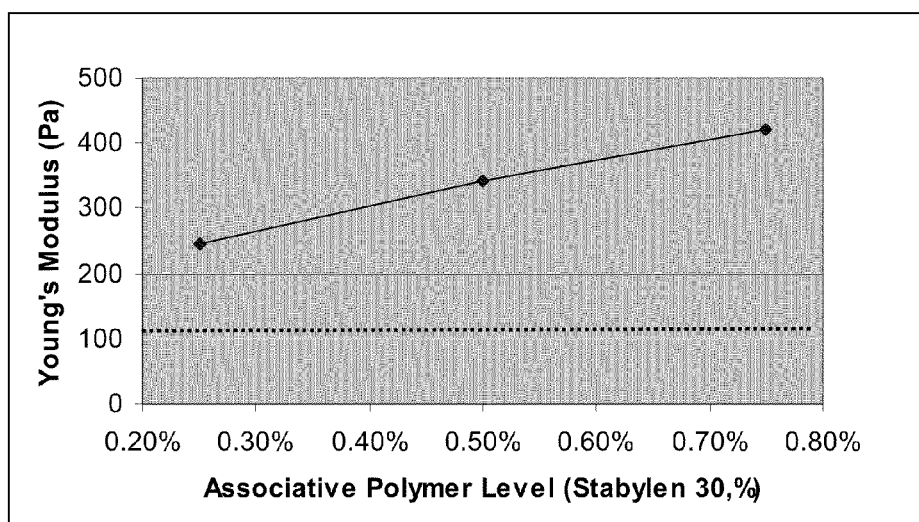
FIG. 4 is a graph that plots the Young's Modulus of a personal care composition of the present invention, as a function of percentage of associative polymer in one embodiment.

Table 5 includes the formulas of examples 5-7 of the present invention and comparative examples E, F, G and H. Examples 5-7 of the present invention show the effectiveness of associative polymer in the lamellar cleansing phase. Examples 5-7 of the present invention show the synergy of associative polymer in combination with a low HLB emulsifier in the lamellar cleansing phase. FIG. 4 is a graph that plots the Young's Modulus of a personal care composition of the present invention, as a function of percentage of associative polymer. FIG. 4 shows there is a significant effect on stability of the composition as the level of associative polymer is raised within the composition.

Figure 3:
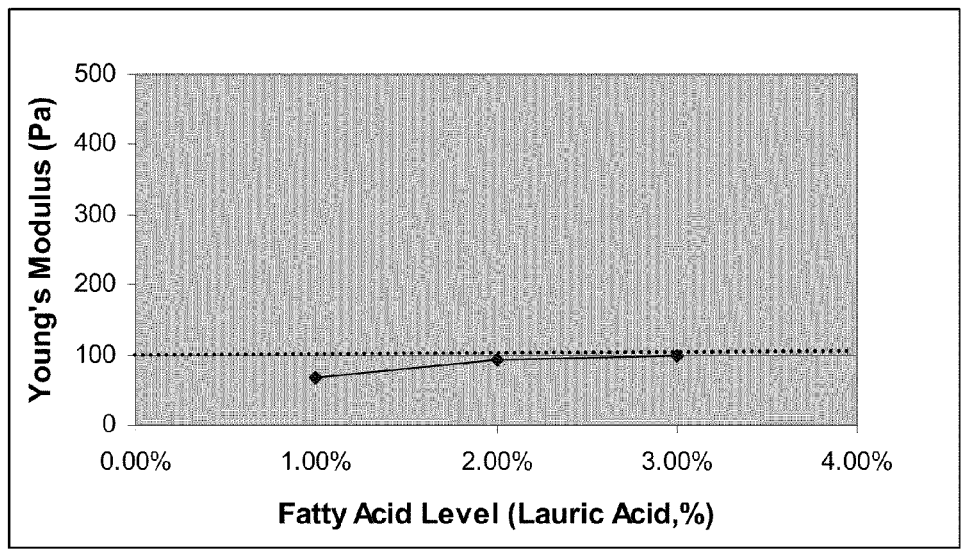
FIG. 3 is a graph that plots the Young's Modulus of a personal care composition of the comparative examples, as a function of percentage of fatty acid structurant.

Comparative example E, F and G show the effect of fatty acid structurants on Young's modulus. As shown in FIG. 2, the fatty acid structurants have less affect on stability, as compared to associative polymers, as a structurant. As the level of fatty acid structurant is increased within the composition, the Young's modulus is minimally affected. Moreover, it is well known that use of increased levels of fatty acid structurants may negatively impact on lather volume, as shown in FIG. 3B of U.S. Pat. No. 6,906,016 issued to Villa.

Figure 5:
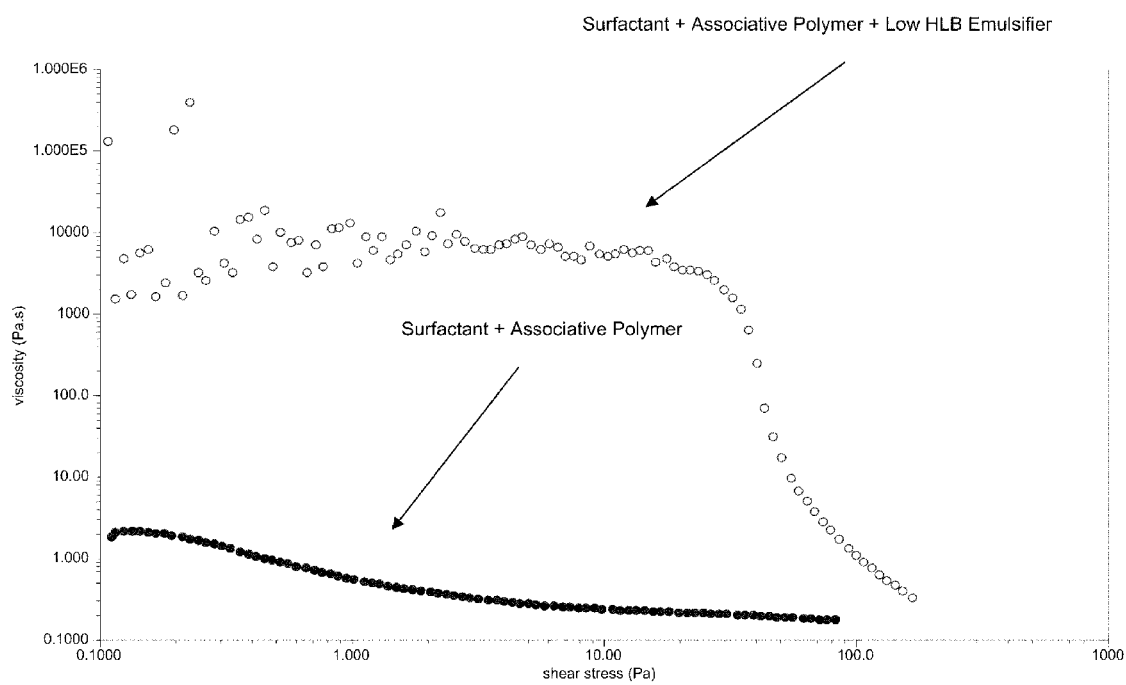
FIG. 5 is a graph that plots the rheology profile of a personal care composition of the present invention using a combination of an associative polymer and a low HLB emulsifier vs. a comparative example using an associative polymer only without low HLB emulsifier in the present surfactant systems.

Comparative example H shows that effect of associative polymers in formulas without the addition of a low HLB emulsifier. The formula of comparative example H includes an associative polymer, acrylates/vinyl isodecanoate, and does not include a low HLB emulsifier. Comparative example H was not structured or stable. The combination of surfactant with the associative polymer, acrylates/vinyl isodecanoate, alone is compared against the combination of the associative polymer, acrylates/vinyl isodecanoate, with a low HLB emulsifier, in FIG. 5. At a relatively low usage level, the associative polymer, acrylates/vinyl isodecanoate, alone does not stabilize or structure in the present surfactant compositions. It is believed that the low HLB emulsifier helps the alignment of surfactant tail group to create a tighter packing of surfactants around the hydrophobic region of the associative polymer, acrylates/vinyl isodecanoate. As a result, there is a very large synergy using a combination of an associative polymer such as acrylates/vinyl isodecanoate and a low HLB emulsifier as shown in FIG. 5.

TABLE 6

Inventive Example 7 and Comparative Examples I and J.

|  | Inventive Example 8 | Comparative Example I | Comparative Example J |
| --- | --- | --- | --- |
| I: Cleansing Phase Composition | | | |
| Total Lathering Surfactant Component in Cleansing Phase (%) | 15.4 | 15.4% | 15.4% |
| Sodium Trideceth Sulfate [1] | 5.9 | 5.9 | 5.9 |
| Sodium Lauryl Sulfate [2] | 5.9 | 5.9 | 5.9 |
| Sodium Lauroamphoacetate [3] | 3.6 | 3.6 | 3.6 |
| Associative Polymer | | | |
| Acrylates/Vinyl Isodecanoate [4] | 0.25% | — | — |
| Non-associative Polymer | | | |
| Carbomer [5] | — | — | 0.25% |
| Sodium Chloride | 3.3 | 3.3 | 3.3 |
| Trideceth-3 (HLB = 8) [6] | 1.4 | 1.4 | 1.4 |
| Methyl chloro isothiazolinone and methyl isothiazolinone [7] | 0.033 | 0.033 | 0.033 |
| EDTA [8] | 0.15 | 0.15 | 0.15 |
| Sodium Benzoate | 0.2 | 0.2 | 0.2 |
| Citric Acid, titrate (pH = ±0.2) | 5.7 | 5.7 | 5.7 |
| Water | Q.S. | Q.S. | Q.S. |

TABLE 6-continued

Inventive Example 7 and Comparative Examples I and J.

|  | Inventive Example 8 | Comparative Example I | Comparative Example J |
|---|---|---|---|
| II: Benefit Phase Composition |  |  |  |
| Petrolatum [9] | 70 | 70 | 70 |
| Mineral Oil [10] | 30 | 30 | 30 |

[1] sulfated from Iconol TDA-3, available from BASF Corp. to >95% sulfate;
[2] available from Procter & Gamble Co.;
[3] available from Cognis Chemical Corp.;
[4] Stabylen 30 available from 3V;
[5] Carbopol 940 from BF Goodrich;
[6] Iconal TDA-3 available from BASF Corp.;
[7] Kathon CG, available from Rohm & Haas Company, Philadephia, PA;
[8] Dissolvine NA 2x.
[9] G2218 from Sonnerbonn;
[10] Hydrobrite 1000 from Sonnerbonn.

Table 6 include the formulas for example 7 of the present invention and comparative examples I and J. Comparative example I has a formula that includes only typical lamellar structurants (e.g. sodium chloride and trideceth-3) at a surfactant level of about 16% in the presence of a benefit phase. Comparative example J has a formula that includes typical lamellar structurants (e.g. sodium chloride and Trideceth-3) and a non-associative polymer (e.g. Carabopol) at surfactant level of about 16% in the presence of a benefit phase.

TABLE 7

Inventive Example 8 and Comparative Examples I-1, I-2, I-3, J-1, J-2 and J-3

|  | Inventive Examples | | | Comparative Examples | | | | | |
|---|---|---|---|---|---|---|---|---|---|
|  | 8-A | 8-B | 8-C | I-1 | I-2 | I-3 | J-1 | J-2 | J-3 |
| Blending Ratio of Cleansing:Benefit Phase | 95:5 | 90:10 | 85:15 | 95:5 | 90:10 | 85:15 | 95:5 | 90:10 | 85:15 |
| 10 days @ 12° F. 3$^{rd}$ Phase Volume (%) | 0 | 0% | 0 | 29 | 44 | 48 | 26 | 40 | 42 |
| Lamellar Phase Stability (<10% 3$^{rd}$ phase) | Stable | Stable | Stable | Not Stable | Not Stable | Not Stable | Not Stable | Not Stable | Not Stable |

Table 7 includes the stability data for example 7 of the present invention and comparative examples I and J. Comparative example I which includes only typical lamellar structurants (e.g. sodium chloride and trideceth-3) with a surfactant level of about 16% in the presence of a benefit phase; is not stable or structured according to the "Third Phase" Method described below. Comparative example J which includes typical lamellar structurants (e.g. sodium chloride and trideceth-3) with a non-associative polymer (e.g. Carbomer) at surfactant level of about 16% in the presence of a benefit phase; was not stable or structured according to the "Third Phase" method.

TABLE 8

Inventive Examples 9-12

|  | 9 | 10 | 11 | 12 |
|---|---|---|---|---|
| I: Cleansing Phase Composition |  |  |  |  |
| Total Lathering Surfactant | 15.4% | 15.4% | 15.4% | 15.4% |
| Component in Cleansing Phase (%) |  |  |  |  |
| Sodium Trideceth Sulfate [1] | 5.9 | 5.9 | 5.9 | 5.9 |
| Sodium Lauryl Sulfate [2] | 5.9 | 5.9 | 5.9 | 5.9 |
| Sodium Lauroamphoacetate [3] | 3.6 | 3.6 | 3.6 | 3.6 |
| Associative Polymer |  |  |  |  |
| Acrylates/Vinyl Isodecanoate [4] | 0.3% | 0.3% | 0.3% | 0.3% |
| Sodium Chloride | 3.8 | 3.8 | 3.8 | 3.8 |
| Trideceth-3 (HLB = 8) [5] | 1.4 | 1.4 | 1.4 | 1.4 |
| Methyl chloro isothiazolinone and methyl isothiazolinone [6] | 0.033 | 0.033 | 0.033 | 0.033 |
| EDTA [7] | 0.15 | 0.15 | 0.15 | 0.15 |
| Sodium Benzoate | 0.2 | 0.2 | 0.2 | 0.2 |
| Perfume | 1.5 | 1.5 | 1.5 | 1.5 |
| Unisperes NT-2806 Green Beads [8] | — | — | — | 3 |
| Guar hydroxypropyltrimonium chloride [9] | 0.1% |  |  |  |
| Citric Acid, titrate (pH = ±0.2) | 5.7 | 5.7 | 5.7 | 5.7 |
| Water and Minor | Q.S. | Q.S. | Q.S. | Q.S. |
| II: Benefit Phase Composition |  |  |  |  |
| Petrolatum [10] | 70 | 67.2 | 67.2 | 70 |
| Mineral Oil [11] | 30 | 28.8 | 28.8 | 30 |
| Titanium Dioxide [12] | — | 4 | — | — |
| Mica/Titanium Dioxide/ Triethoxy caprylylsilane [13] | — | — | 4 | — |
| III: Surfactant:Benefit Phase Ratio | 90:10 | 90:10 | 90:10 | 90:10 |
| Young's Modulus (Pa) | 79 | — | — | — |

[1] sulfated from Iconol TDA-3, available from BASF Corp. to >95% sulfate;
[2] available from Procter & Gamble Co.;
[3] available from Cognis Chemical Corp.;
[4] Stabylen 30, available from 3V;
[5] Iconol TDA-3 available from BASF Corp.;
[6] Kathon CG, available from Rohm & Haas Company, Philadephia, PA;
[7] Dissolvine NA 2x.
[8] Unisperes from Induchem;
[9] N-Hance 3196 Polymer available from Aqualon;
[10] G2218 from Sonnerbonn;
[11] Hydrobrite 1000 from Sonnerbonn.
[12] SAT-T-CR50 Silicone Treated from US Cosmetics;
[13] Kobopearl Stellar White-11S2 from Kobo Products Inc.

Table 8 includes of examples 9-12 of the present invention which include optional benefit agents, such as polyethylene beads, interference pigments, and hydrophobically modified titanium dioxide. These optional benefit agents can be suspended within the composition due to the stable structure imparted by the combination of structuring system of the present invention.

TABLE 9

Inventive examples 13 and 14

|  | Inventive Examples | |
|---|---|---|
|  | 13 | 14 |
| I: Cleansing Phase Composition | | |
| Total Lathering Surfactant Component in Cleansing Phase (%) | 15.4 | 15.4 |
| Sodium Trideceth Sulfate [1] | 5.9 | 5.9 |
| Sodium Lauryl Sulfate [2] | 5.9 | 5.9 |
| Sodium Lauroamphoacetate [3] | 3.6 | 3.6 |
| Associative Polymer | | |
| Acrylates/Vinyl Isodecanoate [4] | 0.3 | 0.3 |
| Sodium Chloride | 3.8 | 3.3 |
| Trideceth-3 [5] | 1.4 | 1.4 |
| Methyl chloro isothiazolinone and methyl isothiazolinone [6] | 0.033 | 0.033 |
| EDTA [7] | 0.15 | 0.15 |
| Guar hydroxypropyltrimonium chloride [8] | 0.1 | 0.1 |
| Sodium Benzoate | 0.2 | 0.2 |
| Perfume | 1.5 | 1.5 |
| Citric Acid, titrate (pH = ±0.2) | 5.7 | 5.7 |
| Water and Minor | Q.S. | Q.S. |
| II: Benefit Phase Composition | | |
| Versagel MD500 [9] | 91.6 | — |
| Dimethicone Blend [10] | 8.4 | — |
| Dimethicone [11] | — | 100 |
| III: Surfactant:Benefit Phase Ratio | 90:10 | 98:2 |

[1] sulfated from Iconol TDA-3, available from BASF Corp. to >95% sulfate;
[2] available from Procter & Gamble Co.;
[3] available from Cognis Chemical Corp.;
[4] Stabylen 30, available from 3V;
[5] Iconol TDA-3 available from BASF Corp.;
[6] Kathon CG, available from Rohm & Haas Company, Philadelphia, PA;
[7] Dissolvine NA 2x.
[8] N-Hance 3196 Polymer available from Aqualon;
[9] Available from Penereco;
[9] 60% 350 cst and 40% 18,000,000 cst. Dimethicone fluid from General Electric Silicone Products;
[11] A high molecular weight dimethicone with a viscosity of about 300,000 cst available from Dow Corning

TABLE 10

Inventive example 15

| Composition | Comp. Ex. K (w/w %) | Invent. Ex. 15 (w/w %) | Comp. Ex. L (w/w %) |
|---|---|---|---|
| Sodium Trideceth Sulfate (n = 3) [1] | 10.3 | 10.3 | 10.3 |
| Sodium Lauroamphoacetate [2] | 3.2 | 3.2 | 3.2 |
| Trideceth-3 (HLB = 8) [3] | 1.24 | 1.24 | 1.24 |
| Sodium Chloride | 4.22 | 4.22 | 4.22 |
| Guar Hydroproyltrimomium Chloride | 0.53 | 0.53 | 0.53 |
| PEG-90M | 0.13 | 0.13 | 0.13 |
| Acrylates/C10-C30 Alkyl-acrylates crosspolymer (Aqupec SER-300) | | 0.18 | |
| Acrylate copolymer (Aqua SF-1) | | | 0.18 |
| Methyl chloro isothiazolinone and methyl isothiazolinone [4] | 0.03 | 0.03 | 0.03 |

TABLE 10-continued

Inventive example 15

| Composition | Comp. Ex. K (w/w %) | Invent. Ex. 15 (w/w %) | Comp. Ex. L (w/w %) |
|---|---|---|---|
| EDTA [5] | 0.14 | 0.14 | 0.14 |
| Sodium Benzoate | 0.18 | 0.18 | 0.18 |
| Citric Acid, titrate (pH = ±0.2) | 5.7 | 5.7 | 5.7 |
| Soybean Oil | 10 | 10 | 10 |
| Water | Q.S. | Q.S. | Q.S. |
| Total Lathering Surfactant Component in Composition | 13.5% | 13.5% | 13.5% |
| Lamellar Phase Volume (%) | 81% | 80% | 77% |
| Young's Modulus (Pa) | 100.1 | 156.3 | 46.21 |
| Young Modulus Change % vs. No Polymer Control | — | +53% | −53.9% |
| Zero Shear Viscosity (PaS) | 2554 | 4302 | 1136 |
| Zero Shear Viscosity Change % Vs. No Polymer Control | — | +68% | −55% |

[1] available from Stepan Coporation
[2] available from Cognis Chemical Corp.
[3] Iconal TDA-3 available from BASF Corp.
[4] Kathon CG, available from Rohm & Haas Company, Philadelphia, PA;
[5] Dissolvine NA 2x.

Table 10 includes example 15 which illustrates the effectiveness of crosslinked, associative polymers of the current invention. After preparing these compositions, their Lamellar Phase Volume, Young's Modulus, and Zero Shear Viscosity were determined utilizing the methods disclosed herein. The results are captured below in Table 10. Inventive Example 15 showed an increase in Young's Modulus of about 53% while comparative examples K and L showed minimal to negative effect to the structure of the composition. The increase of the Young's modulus is surprising due to the low usage level (about 0.2%) of the associative polymer. It is believed the synergistic behavior is attributed to strong associating interaction between the hydrophobic chain of the polymer and the lamellar vesicles of the surfactant composition.

Examples in Table 1-4 can be prepared using conventional mixing techniques. A Hauschild SpeedMixer (Model DAC400 FV from FlackTek Inc. Landrum, S.C.) is recommended for preparing examples in the present invention. Example A is prepared in the following manner: First, prepare a polymer premix by adding Xanthan gum and Polyetheneoxide into Trideceth-3 with mixing. The structured surfactant can then be prepared using the following order of addition with adequate mixing: water, guar hydroxypopyltrimonium chloride, sodium chloride, sodium lauroamphoacetate, sodium lauryl sulfate, sodium trideceth-3, polymer premix (trideceth-3/xanthan gum/polyox), EDTA, and sodium benzoate. Adjust pH to 5.7 by adding citric. Then add Kathon and keep mixing until homogeneous. Comparative example A-0 to A-6 can be prepared by adding DI water to example A to reach a desired dilution factor with adequate mixing. Comparative examples B-3, C-3, D-3, B-4, C-4, and D-4 are prepared by first diluting example A in DI water to appropriate dilution level. Then add sodium chloride, trideceth-3 and non-associative polymer with adequate mixing. Inventive examples 1-5 can be prepared by first diluting structured surfactant from example A to the desired level. Then, add associative polymers with adequate mixing. The Aculyn polymers are supplied as aqueous dispersion and they are directly added. Stabylen 30 is supplied as a powder and it can be first dispersed in polar oil (soybean oil at 1:3 ratio) for ease of processing. Adjust the final product pH to 5.7 using caustic solution. The final mixture is mixed using a SpeedMixer for one minute at 2800 rpm.

Examples in Table 5-6 can be prepared by the following order of addition with adequate mixing: water, sodium chloride, sodium lauroamphoacetate, sodium lauryl sulfate, sodium trideceth sulfate, trideceth-3, EDTA, sodium benzoate. Adjust pH to 5.7 using citric acid. Add Kathon. Then, slowly add polymer (stablyen or carbopol) with good agitation. For comparative examples with fatty acid as structurant, fatty acid is first melted at 70° C. before incorporation. Adjust the pH using caustic solution to 5.7. The benefit phase is prepared by heating petrolatum to 88° C. and adding mineral oil. Cool the benefit phase to about 43.3° C. and then add the benefit phase to the surfactant phase with mixing. The final mixture is mixed using a SpeedMixer for one minute at 2800 rpm Examples in Table 8 can be prepared by the following order of addition with adequate mixing: water, guar hydroxypropyltrimonium chloride, sodium chloride, sodium lauroamphoacate, sodium lauryl sulfate, sodium trideceth sulfate, trideceth-3, EDTA, sodium benzoate. Adjust pH to 5.7 using citric acid. Add kathon. Slowly add associative polymer (Stabylen 30) with good mixing. Adjust pH to 5.7. Add polyethylene beads. Prepare the benefit phase by heating the petrolatum to 88° C. and add mineral oil. Add titanium dioxide, interference pigment. Cool the benefit phase to about 43.3° C. Add the benefit phase to the surfactant phase with mixing.

Examples in Table 9 can be prepared by the following order of addition with adequate mixing: water, guar hydroxypropyltrimonium chloride, sodium chloride, sodium lauroamphoacate, sodium lauryl sulfate, sodium trideceth sulfate, trideceth-3, EDTA, sodium benzoate. Adjust pH to 5.7 using citric acid. Add kathon. Slowly add associative polymer (Stabylen 30) with good mixing. Adjust pH to 5.7. Prepare the benefit phase by heating the versagel to 40° C. and dimethicone blend. Add the benefit phase into the cleansing phase with good mixing. Keep mixing until homogeneous.

Examples in Table 10 can be prepared by first adding water in a mixing vessel. Then add the following ingredients with continuously mixing: sodium chloride, guar hydroxypropyltrimonium chloride, sodium lauroamphoacetate, sodium trideceth-3 sulfate. Then add the polymer power (Aqupec) in trideceth-3 to form a premix. Add the polymer-trideceth-3 premix into the main mixing vessel with adequate agitation. Aqua SF-1 is an aqueous dispersion and is added directly into the mixing vessel without premixing with trideceth-3. Then add PEG90M, EDTA, and sodium benzoate. Adjust pH by adding citric acid solution (50% active) to pH=5.7±0.2. Then, add Methyl chloro isothiazolinone and methyl isothiazolinone. Keep mixing until homogeneous. The multiphase composition is prepared by adding soybean oil into the surfactant phase composition through a SpeedMixer™ at a speed of 2,000 rpm for 60 seconds.

VIII. TEST METHODS a. Ultracentrifugation Method

The Ultracentrifugation Method is used to determine the percent of a structured domain or an opaque structured domain (e.g., a lamellar phase) that is present in a multiphase personal care composition. The method involves the separation of the composition by ultracentrifugation into separate but distinguishable layers. The multiphase personal care composition of the present invention can have multiple distinguishable layers (e.g. a structured surfactant layer, and a benefit layer).

First, dispense about 4 grams of multiphase personal care composition into Beckman Centrifuge Tube (11×60 mm) Next, place the centrifuge tubes in an Ultracentrifuge (Beckman Model L8-M or equivalent) and ultracentrifuge using the following conditions: 50,000 rpm, 2 hours, and 40° C.

After ultracentrifuging for 18 hours, determine the relative phase volume by measuring the height of each layer visually using an Electronic Digital Caliper (within 0.01 mm) First, the total height is measured as $H_a$ which includes all materials in the ultracentrifuge tube. Second, the height of the benefit layer is measured as $H_b$. Third, the structured surfactant layer is measured as $H_c$. The benefit layer is determined by its low moisture content (less than 10% water as measured by Karl Fischer Titration). It generally presents at the top of the centrifuge tube. The total surfactant layer height ($H_s$) can be calculated by this equation:

$$H_s = H_a - H_b$$

The structured surfactant layer components may comprise several layers or a single layer. Upon ultracentrifugation, there is generally an isotropic layer at the bottom or next to the bottom of the ultracentrifuge tube. This clear isotropic layer typically represents the non-structured micellar surfactant layer. The layers above the isotropic phase generally comprise higher surfactant concentration with higher ordered structures (such as liquid crystals). These structured layers are sometimes opaque to naked eyes, or translucent, or clear. There is generally a distinct phase boundary between the structured layer and the non-structured isotropic layer. The physical nature of the structured surfactant layers can be determined through microscopy under polarized light. The structured surfactant layers typically exhibit distinctive texture under polarized light. Another method for characterizing the structured surfactant layer is to use X-ray diffraction technique. Structured surfactant layer display multiple lines that are often associated primarily with the long spacings of the liquid crystal structure. There may be several structured layers present, so that $H_c$ is the sum of the individual structured layers. If a coacervate phase or any type of polymer-surfactant phase is present, it is considered a structured phase.

Finally, the structured domain volume ratio is calculated as follows:

$$\text{Structured Domain Volume Ratio} = H_c/H_s \times 100\%$$

If there is no benefit phase present, use the total height as the surfactant layer height, $H_s = H_a$.

b. Yield Stress, Young's Modulus, and Zero Shear Viscosity Method

The Yield Stress and Zero Shear Viscosity of a phase of the present composition, can be measured either prior to combining in the composition, or after combining in the composition by separating the phase by suitable physical separation means, such as centrifugation, pipetting, cutting away mechanically, rinsing, filtering, or other separation means.

A controlled stress rheometer such as a TA Instruments AR2000 Rheometer is used to determine the Yield Stress and Zero Shear Viscosity. The determination is performed at 25° C. with the 4 cm diameter parallel plate measuring system and a 1 mm gap. The geometry has a shear stress factor of 79580 m$^{-3}$ to convert torque obtained to stress. Serrated plates can be used to obtain consistent results when slip occurs.

First a sample of the phase is obtained and placed in position on the rheometer base plate, the measurement geometry (upper plate) moving into position 1 mm above the base plate. Excess phase at the geometry edge is removed by scraping after locking the geometry. If the phase comprises particles discernible to the eye or by feel (beads, e.g.) which are larger than about 150 microns in number average diameter, the gap setting between the base plate and upper plate is increased to the smaller of 4 mm or 8-fold the diameter of the 95$^{th}$ volume percentile particle diameter. If a phase has any particle larger than 5 mm in any dimension, the particles are removed prior to the measurement.

The determination is performed via the programmed application of a continuous shear stress ramp from 0.1 Pa to 1,000 Pa over a time interval of 4 minutes using a logarithmic progression, i.e., measurement points evenly spaced on a logarithmic scale. Thirty (30) measurement points per decade of stress increase are obtained. Stress, strain and viscosity are recorded. If the measurement result is incomplete, for example if material flows from the gap, results obtained are evaluated and incomplete data points excluded. The Yield Stress is determined as follows. Stress (Pa) and strain (unitless) data are transformed by taking their logarithms (base 10). Log(stress) is graphed vs. log(strain) for only the data obtained between a stress of 0.2 Pa and 2.0 Pa, about 30 points. If the viscosity at a stress of 1 Pa is less than 500 Pa-sec but greater than 75 Pa-sec, then log(stress) is graphed vs. log(strain) for only the data between 0.2 Pa and 1.0 Pa, and the following mathematical procedure is followed. If the viscosity at a stress of 1 Pa is less than 75 Pa-sec, the zero shear viscosity is the median of the 4 highest viscosity values (i.e., individual points) obtained in the test, the yield stress is zero, and the following mathematical procedure is not used. The mathematical procedure is as follows. A straight line least squares regression is performed on the results using the logarithmically transformed data in the indicated stress region, an equation being obtained of the form:

$$\text{Log(strain)}=m*\text{Log(stress)}+b \quad (1)$$

Using the regression obtained, for each stress value (i.e., individual point) in the determination between 0.1 and 1,000 Pa, a predicted value of log(strain) is obtained using the coefficients m and b obtained, and the actual stress, using Equation (1). From the predicted log(strain), a predicted strain at each stress is obtained by taking the antilog (i.e., $10^x$ for each x). The predicted strain is compared to the actual strain at each measurement point to obtain a % variation at each point, using Equation (2).

$$\text{\% variation}=100*(\text{measured strain}-\text{predicted strain})/\text{measured strain} \quad (2)$$

The Yield Stress is the first stress (Pa) at which % variation exceeds 10% and subsequent (higher) stresses result in even greater variation than 10% due to the onset of flow or deformation of the structure.

The Young's Modulus (Pa) is obtained by graphing the Stress (Pa) vs. Strain (unitless). Young's modulus is derived from the slope of the regression line of the initial linear region between Stress vs. Strain graph. Structured surfactant compositions in the present invention typically exhibit linear region in the strain range of 0 to about 0.05.

The Zero Shear Viscosity is obtained by taking a first median value of viscosity in Pascal-seconds (Pa-sec) for viscosity data obtained between and including 0.1 Pa and the Yield Stress. After taking the first median viscosity, all viscosity values greater than 5-fold the first median value and less than 0.2× the median value are excluded, and a second median viscosity value is obtained of the same viscosity data, excluding the indicated data points. The second median viscosity so obtained is the Zero Shear Viscosity.

c. The Shear Index (n) and Consistency Value (K)

The Shear Index (n) and Consistency Value (K) are known and accepted means for reporting the viscosity profile of materials having a viscosity that varies with applied shear rate using a Power Law model.

Viscosity of a phase can be measured by applying a shear stress and measuring the shear rate using a rheometer, such as a TA Instruments AR2000 (TA Instruments, New Castle, Del., USA 19720). Viscosity is determined at different shear rates in the following manner. First, the benefit phase is obtained. If there exists more than one distinct (immiscible, e.g.) benefit phase in the composition, such as for example a silicone oil phase and a hydrocarbon phase, they are preferably prepared separately and/or separated from each other, and evaluated separately from each other, although certain benefit phases which are mixtures such as emulsions can be evaluated as mixtures, in addition to evaluating the individual benefit phases individually.

For measurement, a 40 mm diameter parallel plate geometry with a gap of 1 mm is used unless there are particles greater than 0.25 mm, in which case a gap of 2 mm is used. The rheometer uses standard parallel plate conventions to report shear rate at the edge as shear rate of the test; and converts torque to stress using the factor $2/(\pi R^3)$. Using a spatula, a sample comprising a small excess of the benefit phase is loaded onto the rheometer base plate which is at 25° C., the gap is obtained, and excess composition outside the top measurement geometry is removed, locking the top plate in position during the removal of excess sample. The sample is equilibrated to the base plate temperature for 2 minutes. A preshear step is performed comprising 15 seconds of shear at a shear rate of 50 inverse seconds (1/sec). As is known to one skilled in the art, the shear rate with a parallel plate geometry is expressed as the shear rate at the edge, which is also the maximum shear rate. After the preshear step, the measurement is performed, which comprises ramping the stress from 10 Pa to 1,000 Pa over a 2.0 minute interval at 25° C., while collecting 60 viscosity data points, in an evenly spaced linear progression. A shear rate of at least 500 1/seconds is obtained in the test, or the test is repeated with a fresh sample of the same component with a higher final stress value, maintaining the same rate of stress increase per time, until a shear rate of at least 500 1/sec is obtained during the measurement period. During the measurement, observe the sample to make certain the area under the top parallel plate is not evacuated of sample at any edge location during the measurement, or the measurement is repeated until a sample remains for the duration of the test. If after several trials a result cannot be obtained due to sample evacuation at the edge, the measurement is repeated leaving an excess reservoir of material at the edge (not scraping). If evacuation still cannot be avoided, a concentric cylinder geometry is used with a large excess of sample to avoid air pockets during loading. The results are fitted to the power law model by selecting only the data points between 25-500 1/sec shear rate, viscosity in Pa-s, shear rate in 1/sec, and using a least squares regression of the logarithm of viscosity vs. the logarithm of shear rate to obtain values of K and n according to the Power Law equation:

$$\mu=K(\gamma')^{(n-1)}$$

The value obtained for the log-log slope is (n−1) where n is the Shear Index and the value obtained for K is the Consistency Value, expressed in units of in Pa-s.

d. The "Third-Phase" Method for Determining Structured Surfactant Stability

The "Third-Phase" Method is used to determine structured surfactant phase stability in a personal care compositions. The method involves separation of the composition through ultracentrifugation into separate but distinguishable layers. The personal cleansing composition of the present invention can have multiple distinguishable layers, for example an opaque structured surfactant layer, a clear "third-phase" layer, and benefit phase layers.

The rapid stability aging protocol involves placing the stability sample at 120° F. (48.9° C.) for 10 days. After rapid aging stability testing, transfer about 4 grams of the composition into a Beckman Centrifuge Tube (11×60 mm) Place the centrifuge tube in a Beckman LE-80 Ultracentrifuge and operate the Ultracentrifuge under the following conditions: 50,000 rpm, 2 hours, and at 40° C.

After ultracentrifugation, determine the third-phase volume by measuring the height of various surfactant phases using an Electronic Digital Caliper (within 0.01 mm) as shown below. An example is shown below for a cleansing composition comprising Expancel microspheres, petrolatum, mineral oil and a structured surfactant phase.

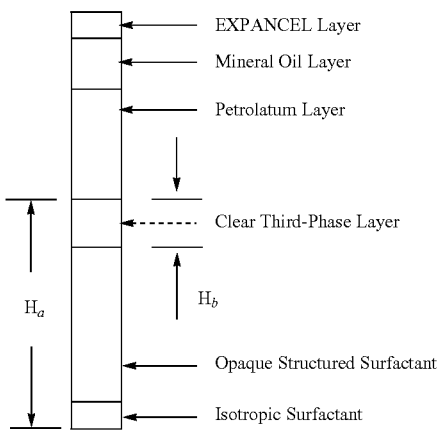

When a density modifier such as Expancel hollow microspheres is used, the very top layer primarily comprises the EXPANCEL microspheres. The second layer from the top is the clear mineral oil layer. The third layer from the top is the petrolatum layer. The layers below the petrolatum layers contain aqueous surfactant and are characterized as follows: $H_a$ is the height of all the aqueous and/or aqueous surfactant layers and $H_b$ is the height of the clear "third-phase" layer just below the petrolatum layer. It is important to record the readings within 30 minutes after the Ultracentrifugation is finished to minimize material migration. The third phase volume is calculated as: Third-phase Volume %=$H_b/H_a$*100%

Preferably, the structured surfactant composition comprises less than 5% "third-phase" volume after rapid aging protocol. More preferably, the structured surfactant composition comprises less than 2% "third-phase" volume after rapid aging protocol. Most preferably, the structured surfactant composition comprises less than 1% "third-phase" volume after rapid aging protocol.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   a surfactant phase comprising:
      about 3% to about 12%, by weight of the personal care composition, of a surfactant, the surfactant comprising sodium trideceth sulfate;
      about 4% or less, by weight of the personal care composition, of a co-surfactant;
   a structuring system comprising:
      about 0.05% to about 0.2%, by weight of the personal care composition, of an associative polymer comprising an acrylate/C10-30 alkyl acrylate crosspolymer;
      an electrolyte; and
   a benefit phase comprising about 1% to about 50%, by weight of the personal care composition, of a hydrophobic benefit material.

2. The personal care composition of claim 1, wherein the co-surfactant comprises an amphoteric surfactant, a zwitterionic surfactant, or a mixture thereof.

3. The personal care composition of claim 1, wherein the structuring system further comprises a non-ionic emulsifier.

4. The personal care composition of claim 3, wherein the personal care composition comprises about 0.1% to about 10%, by weight of the personal care composition, of the non-ionic emulsifier.

5. The personal care composition of claim 3, wherein the nonionic emulsifier comprises glyceryl monohydroxystearate, isosteareth-2, trideceth-3, hydroxystearic acid, propylene glycol stearate, PEG-2 stearate, sorbitan monostearate, glyceryl laurate, laureth-2, cocamide monoethanolamine, lauramide monoethanolamine, or a mixture thereof.

6. The personal care composition of claim 1, wherein said personal care composition comprises about 0.1% to about 6%, by weight of the personal care composition, of the electrolyte.

7. The personal care composition of claim 6, wherein the electrolyte comprises an anion comprising phosphate, chloride, sulfate, citrate, or a mixture thereof; and a cation comprising sodium, ammonium, potassium, magnesium, or a mixture thereof.

8. The personal care composition of claim 1, wherein the associative polymer comprises acidic monomers and associative monomers having hydrophobic end groups.

9. The personal care composition of claim 8, wherein the acidic monomers are selected from a group consisting of: sulfate, sulfonate, carboxylate, phosphonate, phosphate, and mixtures thereof.

10. The personal care composition of claim 1, wherein the personal care composition comprises a Young's Modulus of greater than 100.

11. The personal care composition of claim 1, wherein the personal care composition comprises a zero shear viscosity of about 3000 or greater.

12. The personal care composition of claim 1, wherein the hydrophobic benefit material is selected from a group consisting of: soy bean oil, sunflower seed oil, petrolatum, glycerol monooleate, mineral oil, cylceryl mono-oleate, and dimethicone.

13. The personal care composition of claim 1, wherein the personal care composition is substantially free of sodium laureth sulfate.

14. A personal care composition comprising:
a surfactant phase comprising:
about 3% to about 12%, by weight of the personal care composition, of a surfactant, the surfactant comprising sodium trideceth sulfate;
about 4% or less, by weight of the personal care composition, of a co-surfactant;
a structuring system comprising:
about 0.05% to about 0.2%, by weight of the personal care composition, of a crosslinked associative polymer, the crosslinked associative polymer comprising a hydrophobic modification of less than 2%, and the crosslinked associative polymer comprising a C-16 to C-22 alkyl hydrophobic side chain;
an electrolyte; and
a benefit phase comprising about 1% to about 50%, by weight of the personal care composition, of a hydrophobic benefit material.

15. The personal care composition of claim 1, wherein the associative polymer has a hydrophobic modification of about 10% or less.

16. A personal care composition, comprising:
a surfactant phase comprising from about 3% to about 16%, by weight of the personal care composition, of a lathering surfactant;
a structuring system comprising from about 0.05% to about 5%, by weight of the personal care composition, of an associative polymer comprising Aqupec SER-300, Aqupec SER-150, Aqupec HV-701EDR, or a combination thereof; and from about 0.1% to about 6%, by weight of the personal care composition, of an electrolyte; and
a benefit phase comprising from about 1% to about 50%, by weight of the personal care composition, of a benefit material.

17. The personal care composition of claim 16, wherein the structuring system further comprises from about 0.1% to about 10%, by weight of the oral care composition, of a non-ionic emulsifier.

18. The personal care composition of claim 17, wherein the lathering surfactant comprises sodium trideceth sulfate.

19. The personal care composition of claim 18, wherein the non-ionic surfactant comprises trideceth-3.

20. The personal care composition of claim 19, wherein the benefit material comprises petrolatum.

* * * * *